US008167808B2

(12) United States Patent
Sato

(10) Patent No.: US 8,167,808 B2
(45) Date of Patent: May 1, 2012

(54) TREATMENT INSTRUMENT SYSTEM

(75) Inventor: Sunao Sato, Yamato (JP)

(73) Assignee: Olympus Medical Systems Corp., Tokyo (JP)

(*) Notice: Subject to any disclaimer, the term of this patent is extended or adjusted under 35 U.S.C. 154(b) by 1027 days.

(21) Appl. No.: 12/062,054

(22) Filed: Apr. 3, 2008

(65) Prior Publication Data

US 2008/0249416 A1 Oct. 9, 2008

(30) Foreign Application Priority Data

Apr. 5, 2007 (JP) .................. 2007-099893

(51) Int. Cl.
*A61B 17/22* (2006.01)

(52) U.S. Cl. ........ 600/459; 600/437; 600/439; 600/443; 600/473

(58) Field of Classification Search .................. 600/437, 600/445, 454, 473

See application file for complete search history.

(56) References Cited

U.S. PATENT DOCUMENTS

| | | | |
|---|---|---|---|
| 6,238,336 B1 | 5/2001 | Ouchi | |
| 7,621,873 B2* | 11/2009 | Owen et al. | 600/459 |
| 7,934,703 B2* | 5/2011 | Tomono et al. | 261/18.1 |
| 2003/0114732 A1 | 6/2003 | Webler et al. | |
| 2003/0130674 A1* | 7/2003 | Kasahara et al. | 606/159 |
| 2003/0199768 A1* | 10/2003 | Cespedes et al. | 600/473 |
| 2003/0236443 A1* | 12/2003 | Cespedes et al. | 600/29 |
| 2006/0241480 A1 | 10/2006 | Wilk | |

FOREIGN PATENT DOCUMENTS

| | | |
|---|---|---|
| JP | 06-022966 A | 2/1994 |
| JP | 09-019432 A | 1/1997 |
| JP | 2003-299663 A | 10/2003 |
| JP | 2004-267772 | 9/2004 |
| JP | 2005-095590 A | 4/2005 |
| JP | 2006-288755 A | 10/2006 |
| JP | 2007-000463 A | 1/2007 |
| WO | WO 97/17014 | 5/1997 |

OTHER PUBLICATIONS

Japanese Office Action, mailed Dec. 20, 2011, in counterpart Japanese Patent Application No. 2007-099893.

* cited by examiner

*Primary Examiner* — Tse Chen
*Assistant Examiner* — Baisakhi Roy
(74) *Attorney, Agent, or Firm* — Scully, Scott, Murphy & Presser, P.C.

(57) ABSTRACT

A treatment instrument system according to the present invention includes: an endoscope having a treatment instrument channel; an ultrasound probe inserted through the treatment instrument channel of the endoscope; an ultrasound observing apparatus having a blood flow display function and a distance measuring function; a treatment instrument having, at a distal end portion, an ultrasound scattering portion for scattering ultrasound; and an over tube having an endoscope insertion path through which the endoscope can be inserted and a treatment instrument insertion path through which the treatment instrument can be inserted, and having, at a distal end portion, an ultrasound scattering portion for scattering ultrasound.

26 Claims, 22 Drawing Sheets

US 8,167,808 B2

TREATMENT INSTRUMENT SYSTEM

This application claims benefit of Japanese Patent Application No. 2007-099893 filed on Apr. 5, 2007 the contents of which are incorporated by this reference.

BACKGROUND OF THE INVENTION

1. Field of the Invention

The present invention relates to a treatment instrument system, and more particularly to a treatment instrument system suitable for performing a NOTES procedure.

2. Description of the Related Art

In recent years, researches have been advanced on surgery referred to as a NOTES (Natural Orifice Translumenal Endoscopic Surgery) procedure for inserting an endoscope into an abdomen cavity and perforating a wall surface of a natural orifice organ to perform surgery of a target organ, for example, cholecystectomy, and various proposals on endoscopes and treatment instrument systems used for the NOTES procedure have been made as disclosed in, for example, Japanese Patent Laid-Open No. 2004-267772.

In the NOTES procedure, in a step of inserting a treatment instrument from an inside of an organ such as a digestive tract into which an endoscope is inserted, through a wall surface of the organ, treatment is performed by a process in which the wall surface of the organ is first punctured with a puncture needle and penetrated for insufflation to ensure a space on an outside of the organ, and then a treatment instrument such as a T-bar driver is inserted through the wall surface.

In this case, in insertion of the treatment instrument from the inside of the organ through the wall surface of the organ, there has been no means for checking a situation of an insertion region and an insertion direction of the treatment instrument, that is, a situation of an outside of the wall surface of the organ.

As conventional means for checking a situation of an insertion region and an insertion direction of the treatment instrument, means using a rigid endoscope or the like has possibility.

This means is such that, in insertion of a treatment instrument from an inside of an organ through a wall surface of the organ, a rigid endoscope is inserted from an outside of an abdomen cavity, an insertion region or an insertion direction in insertion of the treatment instrument from an inner wall surface is identified while a situation of an outside of a target organ is checked on an optical image of the rigid endoscope, and puncturing with the treatment instrument is performed. Such means ensures safety in insertion of the treatment instrument from the inside of the organ through the wall surface of the organ.

However, in the NOTES procedure, inserting a rigid endoscope into an abdomen cavity as means for checking a situation of an insertion region and an insertion direction of the treatment instrument as described has a problem in terms of less invasiveness.

In the NOTES procedure, surgery of an organ in an abdomen cavity such as cholecystectomy is performed using only an endoscope. As compared with conventional abdominal surgery or laparoscopic surgery, an illumination range and a field of view are limited in surgery by the NOTES procedure. Thus, for reliable treatment without damaging, for example, blood vessels around a target organ or other organs outside the target organ, the surgery by the NOTES procedure needs more skills than the conventional laparoscopic surgery.

SUMMARY OF THE INVENTION

A treatment instrument system according to the present invention includes: an endoscope having a treatment instrument channel; an ultrasound probe inserted through the treatment instrument channel of the endoscope; an ultrasound observing apparatus having a blood flow display function and a distance measuring function; a treatment instrument having, at a distal end portion thereof, an ultrasound scattering portion for scattering ultrasound; and an over tube having an endoscope insertion path through which the endoscope can be inserted and a treatment instrument insertion path through which the treatment instrument can be inserted, and having, at a distal end portion, an ultrasound scattering portion for scattering ultrasound.

A treatment instrument system according to the present invention includes: an ultrasound endoscope having a treatment instrument channel; an ultrasound observing apparatus having a blood flow display function and a distance measuring function; a treatment instrument having, at a distal end portion, an ultrasound scattering portion for scattering ultrasound; and an over tube having an endoscope insertion path through which the ultrasound endoscope can be inserted and a treatment instrument insertion path through which the treatment instrument can be inserted, and having, at a distal end portion, an ultrasound scattering portion for scattering ultrasound.

A treatment instrument system according to the present invention includes: an endoscope having a plurality of treatment instrument channels; an ultrasound probe placed through one of the treatment instrument channels of the endoscope; an ultrasound observing apparatus having a blood flow display function and a distance measuring function; a treatment instrument having, at an distal end portion, an ultrasound scattering portion for scattering ultrasound; and a sheath member having a treatment instrument insertion path through which the treatment instrument can be inserted, having, at a distal end portion, an ultrasound scattering portion for scattering ultrasound, and placed through another one of the treatment instrument channels of the endoscope.

The above and other objects, features and advantages of the invention will become more clearly understood from the following description referring to the accompanying drawings.

DETAILED DESCRIPTION OF THE PREFERRED EMBODIMENTS

Figure 1:
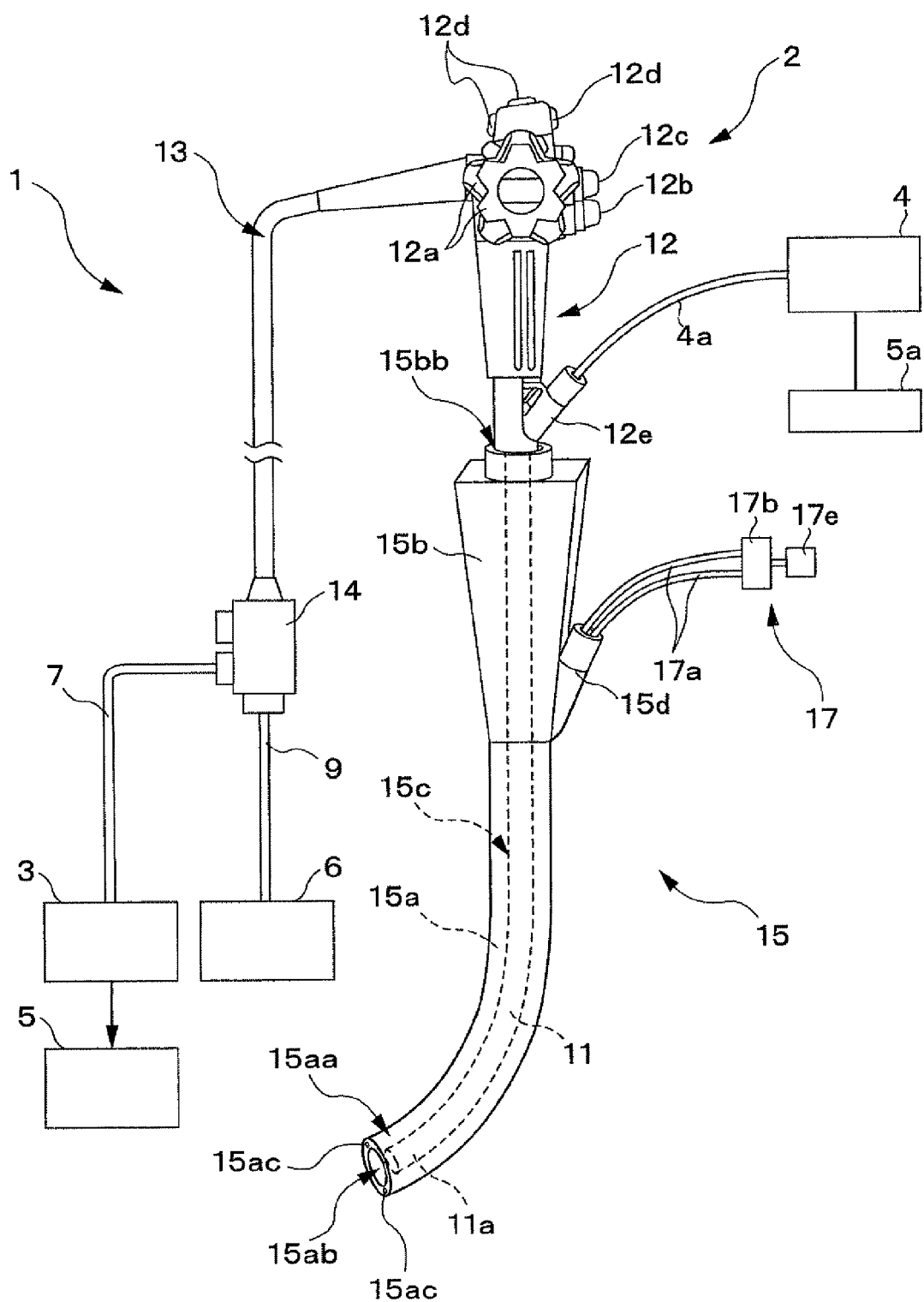
FIG. 1 is a schematic block diagram of an entire configuration of a treatment instrument system according to a first embodiment of the present invention.

Now, the present invention will be described with reference to shown embodiments. Shapes of components, ratios of sizes thereof arrangement positions thereof according to the present invention are not limited to those shown in the drawings.

Figure 2:
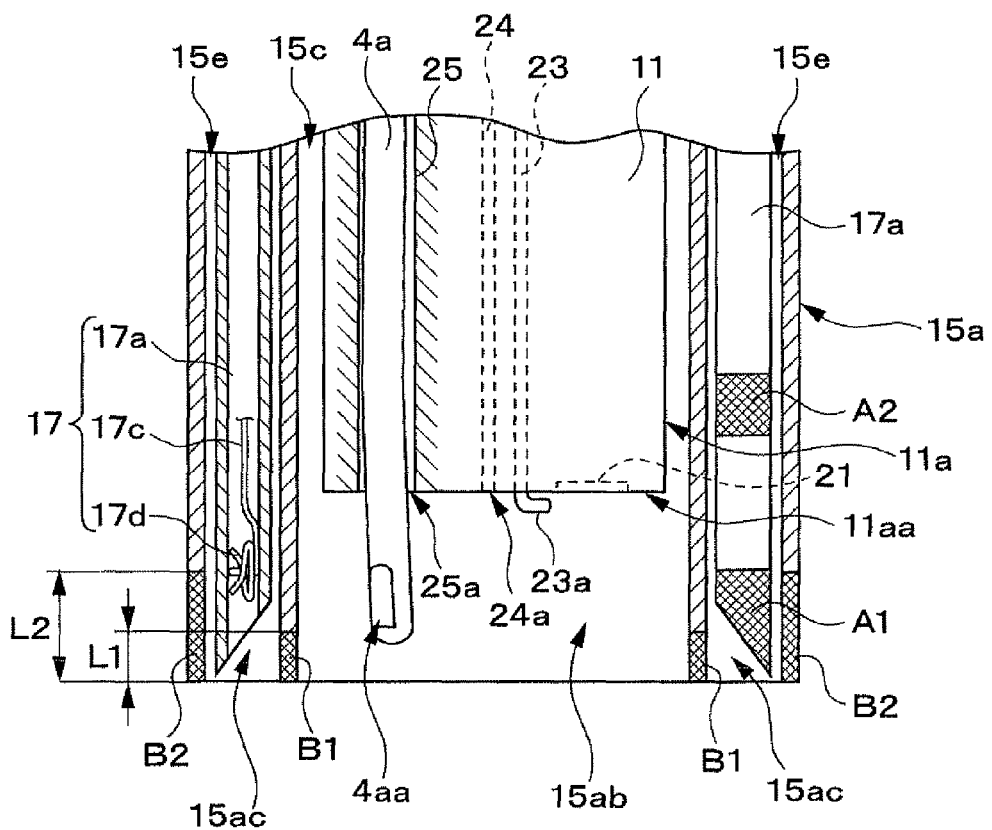
FIG. 2 is an enlarged cross-sectional view of essential portions with distal end portions of an endoscope and an over tube in an endoscope apparatus in the treatment instrument system according to the present embodiment being cut along a surface in an insertion axis direction (a surface along the line [II]-[II] in FIG. 3)
Figure 3:
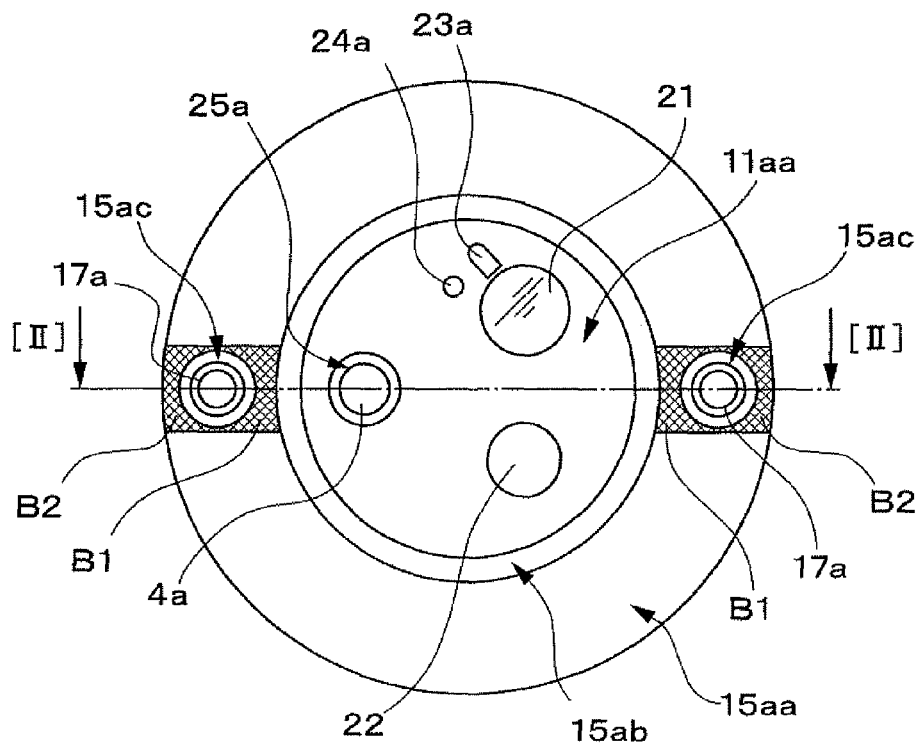
FIG. 3 is a front view of distal end surfaces of the endoscope and the over tube in the present embodiment.

FIG. 1 is a schematic block diagram of an entire configuration of a treatment instrument system according to a first embodiment of the present invention. FIG. 2 is an enlarged cross-sectional view of essential portions in a state where distal end portions of an endoscope and an over tube in an endoscope apparatus in the treatment instrument system in FIG. 1 are cut along a surface in an insertion axis direction (a surface along the line [II]-[II] in FIG. 3). FIG. 3 is a front view of distal end surfaces of the endoscope and the over tube in FIG. 2.

First, the entire configuration of the treatment instrument system according to the first embodiment of the present invention will be described with reference to FIGS. 1, 2 and 3.

The treatment instrument system 1 according to the present embodiment includes: an endoscope apparatus mainly including an endoscope 2 having a treatment instrument channel 25, an endoscope observing apparatus 3, a display apparatus 5, a light source device 6, a video cable 7, and a light source cable 9; an ultrasound observing apparatus 4 having a blood flow display function and a distance measuring function; an ultrasound probe 4a inserted through the treatment instrument channel 25 of the endoscope 2; a treatment instrument (such as a suture treatment instrument or a T-bar driver 17) having, at a distal end portion, ultrasound scattering portions A1 and A2 for scattering ultrasound; and an over tube 15 having an endoscope insertion path 15c through which an insertion portion 11 of the endoscope 2 in the endoscope apparatus can be inserted and a treatment instrument insertion path 15e through which the treatment instrument can be inserted, and having, at a distal end portion, ultrasound scattering portions B1 and B2 for scattering ultrasound.

The endoscope 2 in the endoscope apparatus mainly includes an elongated insertion portion 11 to be inserted into a body, an operation portion 12 connected to a proximal end of the insertion portion 11 for operating the insertion portion 11, an universal cord 13 extending from a side of the operation portion 12, and a connector portion 14 provided at one end of the universal cord 13.

The insertion portion 11 mainly includes, in order from a distal end side, a distal end rigid portion 11a formed of a rigid member, a bending portion connected to a proximal end of the distal end rigid portion 11a and bendably configured, and a flexible tube having one end connected to a proximal end of the bending portion and the other end connected to a distal end of the operation portion 12, and having a small diameter, a long length and flexibility.

An image pickup unit (not shown) for observation by the endoscope is provided at a distal end of the distal end rigid portion 11a. The image pickup unit includes an observation optical system member, an illumination optical system member, and an image pickup device, and is configured to obtain image pickup signals contributing to generating image signals for optically picking up images of an inner wall surface of a luminal organ such as a digestive tract and displaying endoscopic images for observation.

For this purpose, as shown in FIGS. 2 and 3, in a distal end surface 11aa of the distal end rigid portion 11a, an observation window 21 (shown by a dotted line in FIG. 2) and an illumination window 22 (not shown in FIG. 2) are provided. In the distal end surface 11aa, a water feeding nozzle 23a, a suction air feeding opening 24a, or the like are formed around the observation window 21.

The water feeding nozzle 23a and the suction air feeding opening 24a are connected to a water feeding duct 23 and an air feeding duct 24. The water feeding duct 23 and the air feeding duct 24 are placed from the distal end surface 11aa of the insertion portion 11 through the insertion portion 11 and the operation portion 12 to a water feeding apparatus (not shown) provided in the endoscope observing apparatus 3 via the universal cord 13 and the connector portion 14.

The operation portion 12 includes, as shown in FIG. 1, operation members for various operations of the endoscope 2 such as an angle knob 12a that is an operation member for vertically and laterally bending the bending portion of the insertion portion 11, an air/water feeding button 12b for feeding air and water, a suction button 12c for a suction operation, and a plurality of operation members 12d for various operations such as switching displays of the display apparatus 5 or giving freeze instructions or release instructions of display images.

The operation portion 12 is provided with a treatment instrument insertion opening 12e at a distal end thereof in a protruding manner, which is an insertion opening for inserting the ultrasound probe 4a or a treatment instrument of various types through the treatment instrument channel 25 in the insertion portion 11 and introducing the treatment instrument into the body in use of the endoscope 2.

As described above, the universal cord 13 is provided to extend from the side of the operation portion 12, through which a plurality of signal lines that transmit electrical signals or optical fiber cables for illumination light are placed. At a distal end portion of the universal cord 13, the connector portion 14 is provided for ensuring connections between the endoscope 2 and the endoscope observing apparatus 3 and the light source device 6, respectively.

The endoscope observing apparatus 3 is image processing means for driving and controlling the image pickup device in the image pickup unit of the endoscope 2, thus receiving image pickup signals transmitted from the image pickup device to perform various signal processings and generate video signals for endoscope observation images.

The display apparatus 5 receives the video signals generated by the endoscope observing apparatus 3 to display corresponding endoscopic images for observation.

The light source device 6 supplies illumination light to the endoscope 2.

The video cable 7 is a connecting cable for electrically connecting between the endoscope observing apparatus 3 and the endoscope 2.

The light source cable 9 is an optical fiber cable including a bundle of optical fibers for connecting between the light source device 6 and the endoscope 2.

Into the treatment instrument insertion opening 12e provided in the operation portion 12 of the endoscope 2, a treatment instrument of various types such as the ultrasound probe 4a having an ultrasound unit 4aa for generating video signals displayed as ultrasound tomograms, a perforating instrument that is a needle type treatment instrument for an endoscope, or a surgical treatment instrument can be inserted. The treatment instrument insertion opening 12e communicates with the treatment instrument channel 25 formed through the insertion portion 11 to a distal end opening 25a provided in the distal end surface 11aa of the distal end rigid portion 11a.

As described above, the ultrasound probe 4a is inserted from the treatment instrument insertion opening 12e of the endoscope 2 through the treatment instrument channel 25 for use. The ultrasound probe 4a includes a plurality of ultrasound transducers that transmit and receive ultrasound, arranged to form a ultrasound scanning surface, and the ultrasound unit 4aa that can obtain ultrasound signals contributing to creating tomograms (ultrasound tomograms) of an inside of a body cavity wall is provided in a distal end portion 4b. A proximal end of the ultrasound probe 4a is connected to the ultrasound observing apparatus 4 by a connector. A display apparatus 5a for displaying ultrasound tomograms is connected to the ultrasound observing apparatus 4.

In place of the display apparatus 5a, the ultrasound observing apparatus 4 and the display apparatus 5 may be connected by a predetermined connecting cable to simultaneously display or switch endoscopic images and ultrasound tomograms using the display apparatus 5.

The ultrasound observing apparatus 4 is an ultrasound tomogram signal processing device that drives and controls the ultrasound transducers in the ultrasound unit of the ultrasound probe 4a, thus transmits ultrasound of a predetermined frequency toward an object to be observed, receives electrical signals from the ultrasound transducers, the electrical signals being obtained by receiving ultrasound scattered and reflected by the object to be observed, and performs various signal processings to generate video signals for ultrasound tomograms. The ultrasound observing apparatus 4 has a blood flow display function and a distance measuring function.

The display apparatus 5a receives the video signals generated by the ultrasound observing apparatus 4 to display corresponding ultrasound images for observation.

The insertion portion 11 of the endoscope 2 is used while being inserted through the over tube 15.

The over tube 15 includes a flexible tube 15a having a small diameter, a long length and flexibility and through which the insertion portion 11 of the endoscope 2 is inserted, and a proximal end forming portion 15b connected to a proximal end of the flexible tube 15a.

In a distal end surface 15aa of the flexible tube 15a, a distal end opening 15ab having a large diameter is formed substantially at the center when viewed from a front of the distal end, and treatment instrument insertion openings 15ac each having a small diameter are formed at a peripheral edge of the distal end opening 15ab.

The distal end opening 15ab is formed to have a slightly larger diameter than an outer diameter of the insertion portion 11 inserted through the over tube 15.

The plurality of treatment instrument insertion openings 15ac are circumferentially provided at the peripheral edge of the distal end opening 15ab.

A proximal end opening 15bb is formed substantially at the center of one end of the proximal end forming portion 15b when viewed toward an end surface. Between the proximal end opening 15bb and the distal end opening 15ab, an endoscope insertion path 15c is formed passing through the flexible tube 15a and the proximal end forming portion 15b of the over tube 15.

In the proximal end forming portion 15b, a proximal end insertion path opening 15d is provided so as to protrude outward from a side. Between the proximal end insertion path opening 15d and the treatment instrument insertion opening 15ac in the distal end surface 15aa, a treatment instrument insertion path 15e is formed passing through the flexible tube 15a and the proximal end forming portion 15b of the over tube 15.

In an example in FIG. 3, two treatment instrument insertion paths 15e are provided, and two treatment instrument insertion openings 15ac thereof are placed at positions 180° apart and symmetrically opposite to each other.

At a peripheral edge of the treatment instrument insertion opening 15ac formed in the distal end surface of the flexible tube 15a of the over tube 15, ultrasound scattering portions B1 and B2 for scattering ultrasound are provided in a predetermined range. As shown in FIG. 3, the ultrasound scattering portion B1 refers to an area at the peripheral edge of the treatment instrument insertion opening 15ac and closer to the distal end opening 15ab in the flexible tube 15a. Also as shown in FIG. 3, the ultrasound scattering portion B2 refers to an area at the peripheral edge of the treatment instrument insertion opening 15ac and on an outer peripheral side of the flexible tube 15a. In the present embodiment, the ultrasound scattering portions B1 and B2 are formed only at an area of the peripheral edge of the treatment instrument insertion opening 15ac. In the present embodiment, an example is shown in which the ultrasound scattering portions B1 and B2 are formed at an area entirely around the outer periphery of the treatment instrument insertion opening 15ac when viewed from the front of the distal end surface 15aa of the over tube 15.

As shown in FIG. 2, the ultrasound scattering portions B1 and B2 are each provided in a predetermined range in an insertion direction of the treatment instrument insertion path 15e from the treatment instrument insertion opening 15ac toward the proximal end. In this case, a longitudinal range (in the insertion direction) of the ultrasound scattering portion B1 is set to be smaller than a longitudinal range of the ultrasound scattering portion B2. Specifically, the range is set so that a relationship of L1<L2 is satisfied, where L1 is a length of the longitudinal range of the ultrasound scattering portion B1, and L2 is a length of the longitudinal range of the ultrasound scattering portion B2 in FIG. 2.

Into the treatment instrument insertion path 15e of the over tube 15, a treatment instrument of various types, for example, a T-bar driver 17 that is a suture treatment instrument is to be inserted.

The T-bar driver 17 that is a suture treatment instrument has a configuration described below. Specifically, the T-bar driver 17 is inserted from the proximal end insertion path opening 15d in the over tube 15, inserted through each of a plurality of (two in the present embodiment) treatment instrument insertion paths 15e, and placed so as to be protruded from and retracted into the distal end opening 15ab.

The T-bar driver 17 includes a puncture needle 17a (two puncture needles 17a in the present embodiment) that is constituted by a flexible elongated tube, has a distal end formed into a sharp needle, and houses a suturing instrument (such as a suture thread 17c and a T-bar 17d) in a distal end portion, a control box 17b connected to a proximal end portion of the puncture needle 17a for controlling a protruding and retracting operation of the puncture needle 17a or the suturing instrument, and a gas/drug supplier 17e that is connected to the control box 17b for supplying gas (for example, carbon dioxide), a drug, degassed water or physiologic saline as an ultrasound transmission medium via a hollow portion of the puncture needle 17a into an abdomen cavity.

On an outer peripheral surface of a distal end portion of the puncture needle 17a, a plurality of (two in the present embodiment) ultrasound scattering portions A1 and A2 for scattering ultrasound are provided at a predetermined distance apart in a long axis direction of the puncture needle 17a. The ultrasound scattering portion A1 is provided on an outer peripheral surface of a most distal end portion of the puncture needle 17a. The ultrasound scattering portion A2 is a second ultrasound scattering portion provided at a predetermined distance from the ultrasound scattering portion A1. Specifically, the second ultrasound scattering portion A2 is provided for identifying a guide for a puncture depth of the puncture needle 17a. Thus, a distance between the ultrasound scattering portion A1 and the second ultrasound scattering portion A2 is set according to types of treatment and surgery.

In the present embodiment, the ultrasound scattering portions A1 and A2 are formed in respective positions at an area entirely around a peripheral edge of the puncture needle 17a. In FIG. 2, the puncture needle 17a inserted into the treatment instrument insertion path 15e in the right half is shown in a side view rather than a cross-sectional view so as to show a side state of the puncture needle 17a (the same for FIGS. 12 and 13).

An outline of a process of surgery of an organ in an abdomen cavity, for example, cholecystectomy by a NOTES procedure using the treatment instrument system 1 thus configured according to the present embodiment will be now described with reference to FIGS. 4 to 13.

Figure 4:
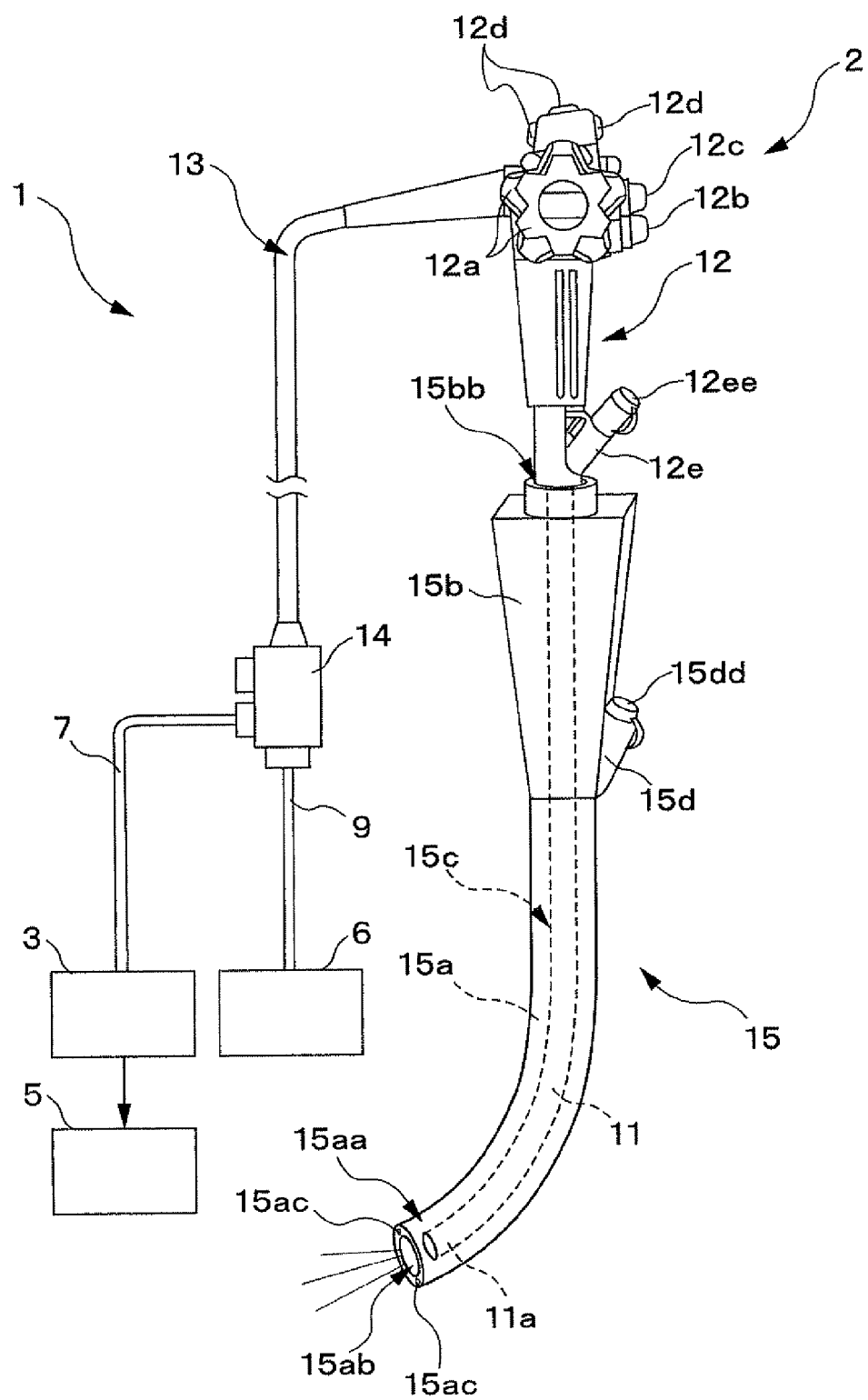
FIG. 4 shows a process of surgery of an organ in an abdomen cavity (cholecystectomy) by a NOTES procedure using the treatment instrument system according to the present invention and shows a system configuration in insertion of the endoscope.

First, as shown in FIG. 4, the endoscope 2 is placed through the over tube 15. Specifically, the distal end surface 11aa of the insertion portion 11 of the endoscope 2 is inserted from the proximal end opening 15bb in the over tube 15, and the insertion portion 11 is placed through the endoscope insertion path 15c. At this time, the distal end surface 11aa of the insertion portion 11 is placed not to protrude outward from the distal end opening 15ab in the over tube 15. In this state, no treatment instrument is placed in the treatment instrument insertion opening 12e of the endoscope 2, and a predetermined lid member 12ee is placed on the opening. Similarly, the suture treatment instrument 17 or the like is not placed in the treatment instrument insertion path 15e of the over tube 15, and a predetermined lid member 15dd is placed on the proximal end insertion path opening 15d as shown in FIG. 4.

At this time, the puncture needle 17a of the suture treatment instrument 17 may be inserted from the proximal end insertion path opening 15d as shown in FIG. 1, and the puncture needle 17a may be placed through the treatment instrument insertion path 15e of the flexible tube 15a of the over tube 15. In the description below, however, as shown in FIG. 4, the puncture needle 17a or the like is not placed in the over tube 15 at this time, but the suture treatment instrument 17 is inserted from the proximal end insertion path opening 15d and placed through the treatment instrument insertion path 15e at predetermined timing thereafter (details will be described later).

In the state in FIG. 4, that is, in the state where the endoscope 2 is placed through the over tube 15, the flexible tube 15a is inserted through a natural orifice, for example, an oral cavity of a subject (patient) to undergo surgery into a target luminal organ, for example, a stomach under observation of endoscopic images by the endoscope 2. In this case, an insertion operation of the endoscope 2 is similar to an operation for a flexible endoscope examination generally performed, and is performed using an operation member of the operation portion 12.

Figure 5:
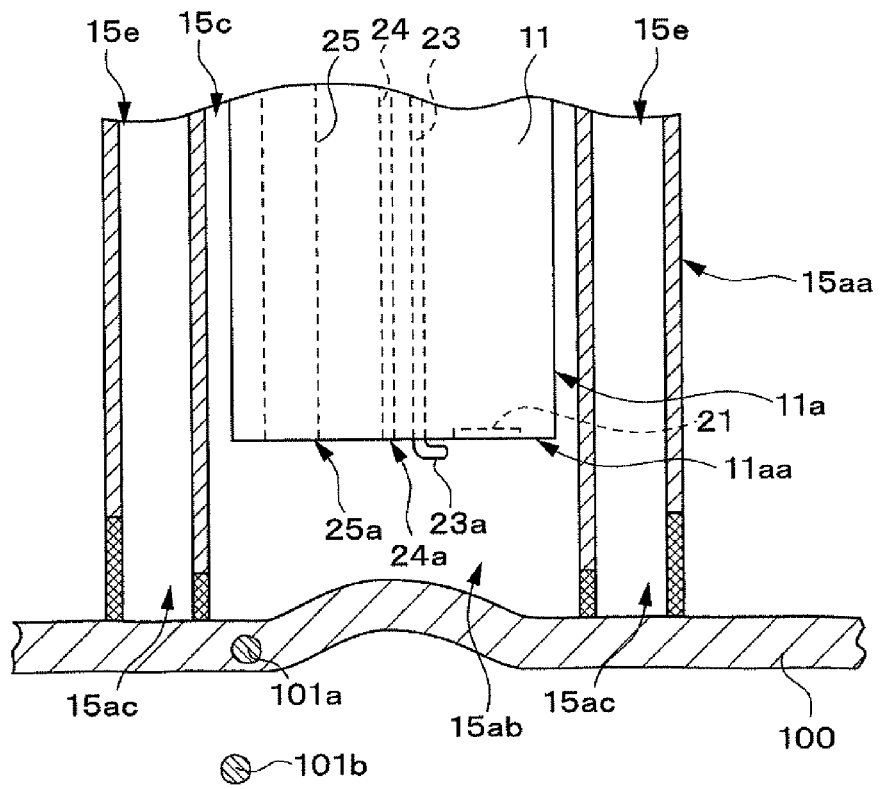
FIG. 5 shows a state where the distal end portion of the over tube abuts against a stomach wall when a flexible tube of the over tube in the treatment instrument system according to the present embodiment is inserted into a luminal organ.

FIG. 5 is a conceptual view of a state where the distal end surface 15aa of the over tube 15 abuts against a stomach wall 100 when the flexible tube 15a of the over tube 15 is inserted into a luminal organ.

As shown in FIG. 5, in the state where the distal end surface 15aa of the over tube 15 abuts against the stomach wall 100, an operator operates the suction button 12c on the operation portion 12 of the endoscope 2 to perform a suction operation. The suction operation causes suction via the suction air feeding opening 24a. Thus, a predetermined region on the stomach wall 100 facing the distal end opening 15ab in the distal end surface 15aa of the over tube 15 is slightly sucked into the distal end opening 15ab, and the stomach wall 100 and the end surface of the distal end surface 15aa of the over tube 15 are brought into watertight contact with each other.

Figure 6:
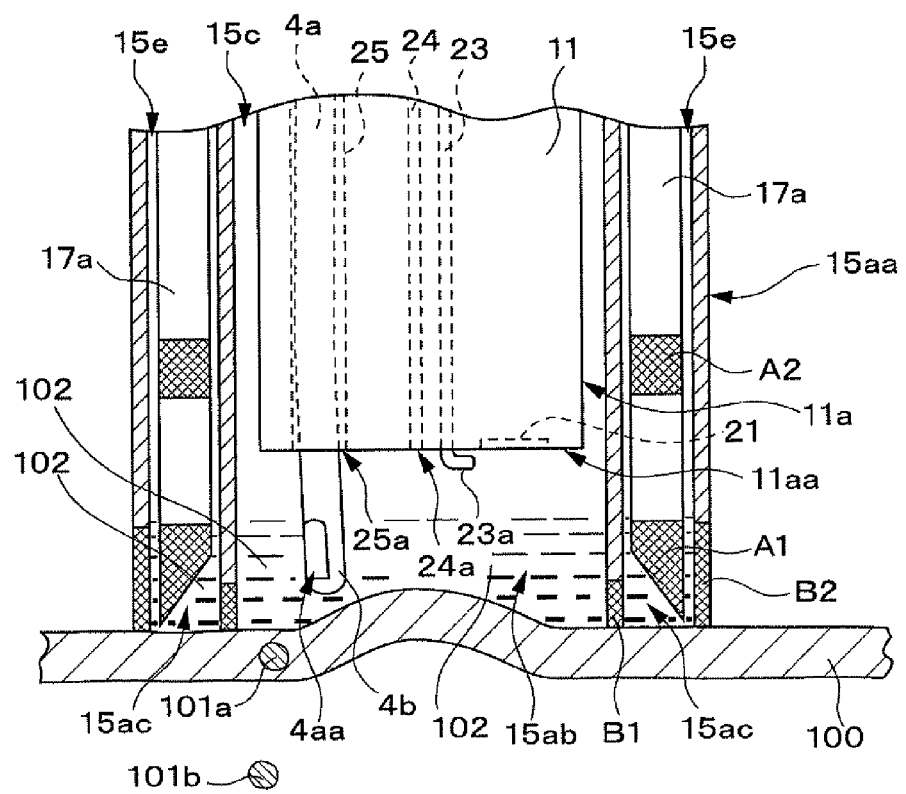
FIG. 6 shows a state where the distal end portion of the over tube in the treatment instrument system according to the present embodiment is filled with a liquid, and a distal end portion of an ultrasound probe is protruded from a distal end surface of a distal end rigid portion of the endoscope.

Then, the operator operates the air/water feeding button 12b on the operation portion 12 of the endoscope 2 to perform a water feeding operation. At this time, the stomach wall 100 and the distal end surface 15aa of the over tube 15 are brought into watertight contact with each other by the above described suction operation, and thus a liquid discharged from the water feeding nozzle 23a by the water feeding operation, for example, degassed water 102 is retained between an inside of the distal end opening 15ab in the distal end surface 15aa of the over tube 15 and the stomach wall 100 as shown in FIG. 6.

Then, the operator removes the lid member 12ee on the treatment instrument insertion opening 12e of the endoscope 2, inserts the distal end portion 4b of the ultrasound probe 4a into the treatment instrument insertion opening 12e, and places the ultrasound probe 4a through the treatment instrument channel 25. At this time, the distal end portion 4b of the ultrasound probe 4a is slightly protruded from the distal end surface 11aa of the distal end rigid portion 11a of the endoscope 2 as shown in FIG. 6 and set so that the ultrasound unit 4aa in the distal end portion 4b is kept submerged in the degassed water 102 retained by the water feeding operation.

In this state, the ultrasound observing apparatus 4 is operated to drive and control the ultrasound probe 4a, and thus an ultrasound tomogram is displayed on the display apparatus 5a. Specifically, in this case, the degassed water 102 retained in the distal end surface 15aa of the over tube 15 serves as an ultrasound transmitting medium.

Using the blood flow display function of the ultrasound observing apparatus 4, blood vessels 101a and 101b and the like of internal organs can be displayed. In FIG. 6, the blood vessel 101b outside the stomach wall 100 is surrounded by tissue or the like in a body cavity though not clearly shown in FIG. 6. In such a state, the blood vessel 101b outside the stomach wall 100 and the ultrasound scattering portions on the over tube 15 and the like can be visually checked by the display apparatus 5a as an ultrasound tomogram.

Further, in this state, the operator removes the lid member 15dd on the proximal end insertion path opening 15d, and inserts the puncture needle 17a of the suture treatment instrument 17 from the proximal end insertion path opening 15d. Then, the puncture needle 17a is inserted through the treatment instrument insertion path 15e of the over tube 15, and the distal end portion of the puncture needle 17a is placed at a position close to the distal end surface 15aa of the over tube 15.

Simultaneously, the operator operates the gas/drug supplier 17e to supply the degassed water 102 through the puncture needle 17a to the distal end portion of the puncture needle 17a. Thus, the degassed water 102 is discharged from the distal end opening in the puncture needle 17a, and the degassed water 102 is retained in the distal end portion of treatment instrument insertion path 15e. Thus, the distal end portion of the puncture needle 17a can be also visually checked on the display apparatus 5a as an ultrasound tomogram. Thus, the operator places the puncture needle 17a so that the distal end portion thereof is not protruded from the most distal end surface of the distal end surface 15aa of the over tube 15 while observing the ultrasound tomogram. The state at this time is shown in FIG. 6.

In the state in FIG. 6, the operator operates the ultrasound probe 4a to direct the ultrasound transmitting and receiving portion of the ultrasound unit 4aa at the distal end portion 4b to a desired observation region. In this case, the distal end portion 4b of the ultrasound probe 4a is operated by general means such as bending in a desired direction using, for example, a raising base (not shown) provided at the distal end rigid portion 11a of the endoscope 2.

Figure 7:
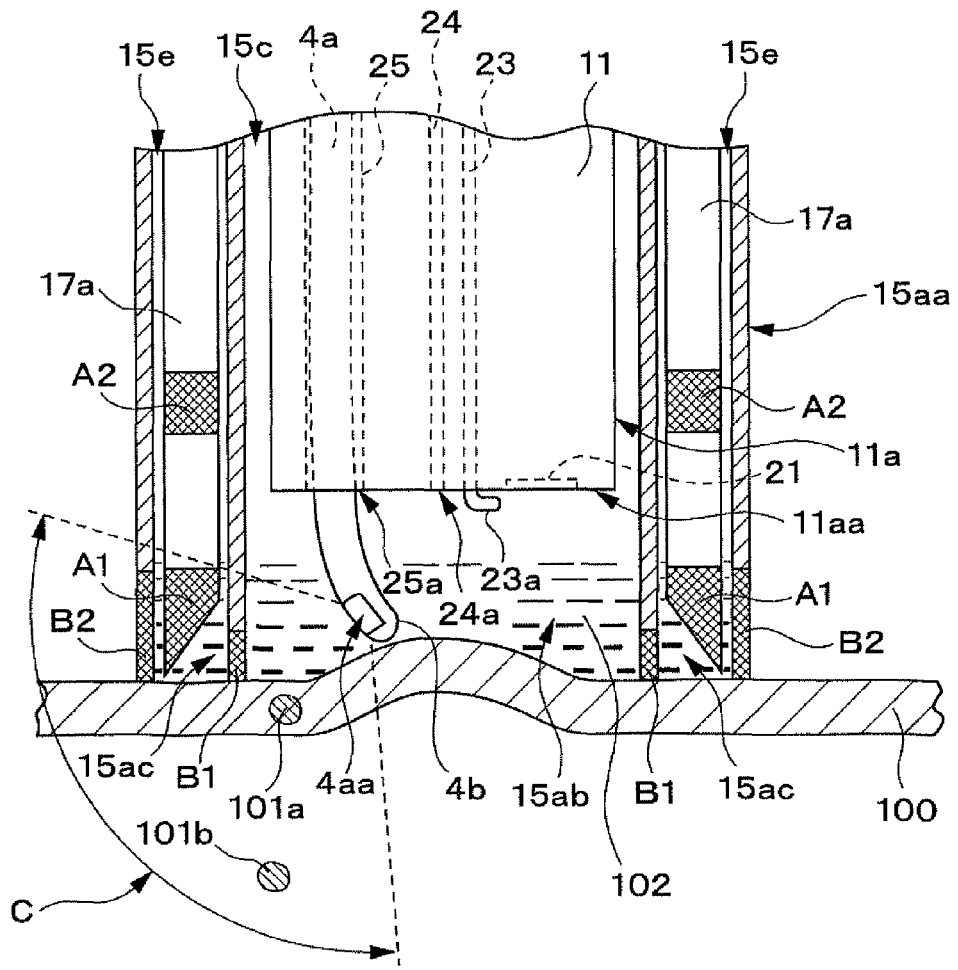
FIG. 7 shows a state where an ultrasound transmitting and receiving portion of an ultrasound unit is directed to a distal end portion of the flexible tube of the over tube with the ultrasound probe in the treatment instrument system according to the present embodiment being driven.

Then, the ultrasound probe 4a is placed shown as in a state in FIG. 7, specifically, placed so that the ultrasound scattering portions B1 and B2 at the distal end portion of the flexible tube 15a of the over tube 15 are included in a field of view of the ultrasound unit 4aa at the distal end portion 4b of the ultrasound probe 4a, that is, the ultrasound scattering portions B1 and B2 are simultaneously displayed on a display portion of the display apparatus 5a. An example of an ultrasound tomogram displayed on the display portion of the display apparatus 5a is shown in FIG. 8.

Figure 8:
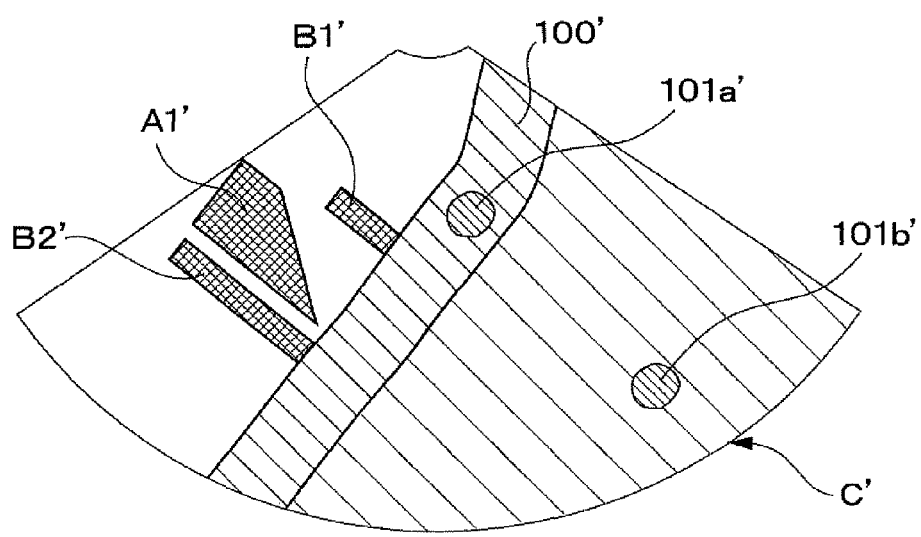
FIG. 8 shows an example of an ultrasound tomogram displayed on a display portion of a display apparatus in the state in FIG. 7.

An image denoted by reference numeral C' in FIG. 8 is an ultrasound tomogram of an area denoted by reference numeral C in FIG. 7. In the ultrasound tomogram, for example, a part of the stomach wall 100 in FIG. 7 is displayed as a tomogram 100' in FIG. 8. Similarly, the blood vessel 101a through the stomach wall 100 is displayed as a tomogram 101a', and the blood vessel 101b through an organ outside the stomach wall 100 (hereinafter referred to as an organ in an abdomen cavity) is displayed as a tomogram 101b'. Besides the internal organs, the ultrasound scattering portions B1 and B2 at the distal end portion of the flexible tube 15a of the over tube 15 inserted into a luminal organ are displayed as tomograms B1' and B2', respectively, and the ultrasound scattering portion A1 on the distal end portion of the puncture needle 17a is displayed as a tomogram A1'.

The operator searches and identifies a puncture position of the puncture needle 17a while observing the above described ultrasound tomograms (FIG. 8; displayed on the display apparatus 5) by the ultrasound probe 4a and endoscopic images (not shown; displayed on the display apparatus 5) by the endoscope 2.

A desirable puncture position of the puncture needle 17a is a position at a predetermined distance on an extension line perpendicular to the stomach wall 100 when viewed from a side of a luminal organ wall, that is, the stomach wall 100, and specifically, a position where there is no organ in an abdomen cavity or blood vessel in a range where the distal end of the puncture needle 17a reaches in puncture of the stomach wall 100.

Specifically, the operator checks a direction substantially perpendicular to an arranging direction of the ultrasound scattering portions B1 (inner side) and B2 (outer side) at the distal end portion of the flexible tube 15a based on the ultrasound tomogram as shown in FIG. 8. Thus, the operator checks whether the direction is a desired puncture direction of the puncture needle 17a. This direction is substantially perpendicular to the wall surface of the stomach wall 100 as described above, and is an advancing direction of the puncture needle 17a. The operator checks whether there is an organ in an abdomen cavity or a blood vessel on the extension line in this direction and in the range which the distal end of the needle reaches. In the example in FIG. 8, it can be checked that there is no organ in an abdomen cavity or blood vessel in the advancing direction of the distal end of the needle, and thus it is found that the puncture of the puncture needle 17a can be started in this state.

On the other hand, though not shown, if it is checked that there is an organ in an abdomen cavity or a blood vessel in the advancing direction of the puncture needle 17a in this stage, and that the position is not a desired puncture start position, the position of the distal end portion of the over tube 15 is moved.

In this case, the operator first operates the air/water feeding button 12b on the operation portion 12 of the endoscope 2 to perform an air feeding operation and the like and thus release the watertight contact between the distal end portion of the over tube 15 and the stomach wall 100 from the state in FIG. 7.

Then, the operator causes the distal end portion of the over tube 15 to abut against the stomach wall 100 at an appropriate region under observation of endoscopic images by the endoscope 2, a suction operation is performed to semi-fix the distal end portion of the over tube 15 on the stomach wall 100, and then a water feeding operation is performed to retain the degassed water 102 in the distal end portion of the over tube 15. Then, the gas/drug supplier 17e is operated to supply the degassed water 102 through the puncture needle 17a to the distal end portion of the puncture needle 17a. Thus, the degassed water 102 is retained also in the distal end portion of the treatment instrument insertion path 15e.

In this state, the ultrasound tomogram by the ultrasound probe 4a is observed to check whether the puncture start position of the puncture needle 17a is proper. Such a series of operations is repeated to identify a proper position for puncture of the puncture needle 17a.

The existence of an organ or a running state of blood vessels on the extension line perpendicular to the wall surface of the stomach wall 100 from the puncture start position thus identified of the puncture needle 17a is checked with the ultrasound tomogram in FIG. 8, the puncture start position and the puncture direction of the puncture needle 17a are checked, and then a puncturing operation of the puncture needle 17a is performed under ultrasound observation. The puncturing operation is performed by the operator performing a predetermined operation of the control box 17b at hand.

Figure 9:
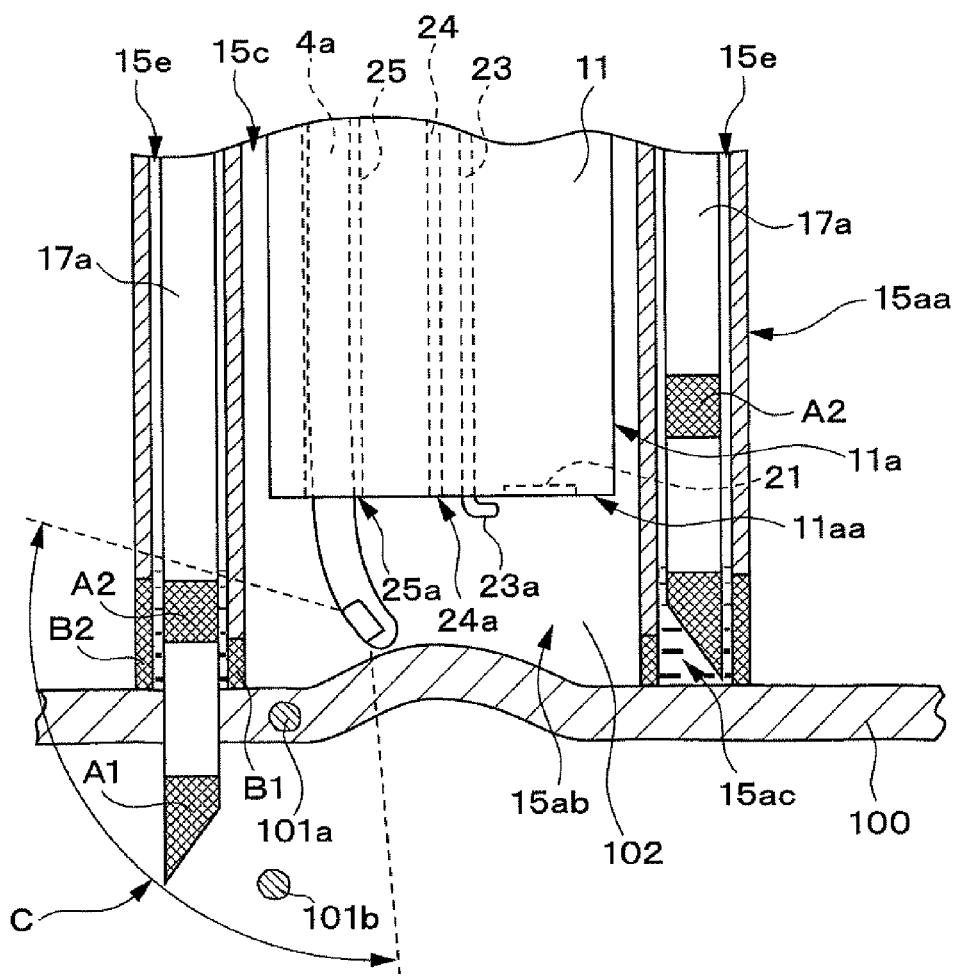
FIG. 9 shows a state where a puncturing operation of a puncture needle is performed and a distal end of the puncture needle penetrates a stomach wall into an abdomen cavity at an identified puncture start position in the treatment instrument system according to the present embodiment.
Figure 10:
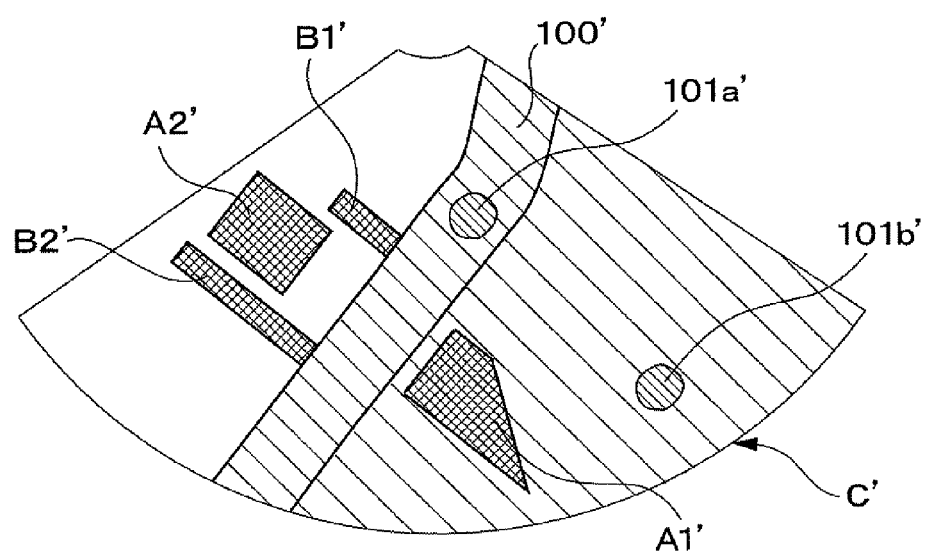
FIG. 10 shows an example of an ultrasound tomogram displayed on the display portion of the display apparatus in the state in FIG. 9.

First, prior to the puncturing operation, the distance measuring function of the ultrasound observing apparatus 4 is used to decide a puncture depth of the puncture needle 17a. Then, the puncturing operation is performed while the ultrasound tomogram being observed. Thus, the distal end of the puncture needle 17a protrudes from the distal end portion of the flexible tube 15a, and penetrates the stomach wall 100 at the identified puncture start position, and is inserted into the abdomen cavity outside the stomach wall 100 as shown in FIG. 9. At this time, an ultrasound tomogram displayed on the display portion of the display apparatus 5a is as shown in FIG. 10.

The puncture needle 17a has, as described above, the ultrasound scattering portion A1 provided at a most distal end portion and the second ultrasound scattering portion A2 provided at a predetermined distance from the ultrasound scattering portion A1. Thus, in a process of performing the puncturing operation of the puncture needle 17a while observing the ultrasound tomogram, it can be first observed that the ultrasound scattering portion A1 (denoted by reference numeral A1' on the tomogram in FIG. 10) penetrates the stomach wall 100 and advances, and when the second ultrasound scattering portion A2 (denoted by reference numeral A2' on the tomogram in FIG. 10) appears on a display screen in the process, the puncture depth can be estimated from the positional relationship between the ultrasound scattering portions. Thus, a position of the tomogram A2' on the screen of the second ultrasound scattering portion A2 is checked, and when the decided puncture depth is reached, the puncturing operation is stopped.

Figure 11:
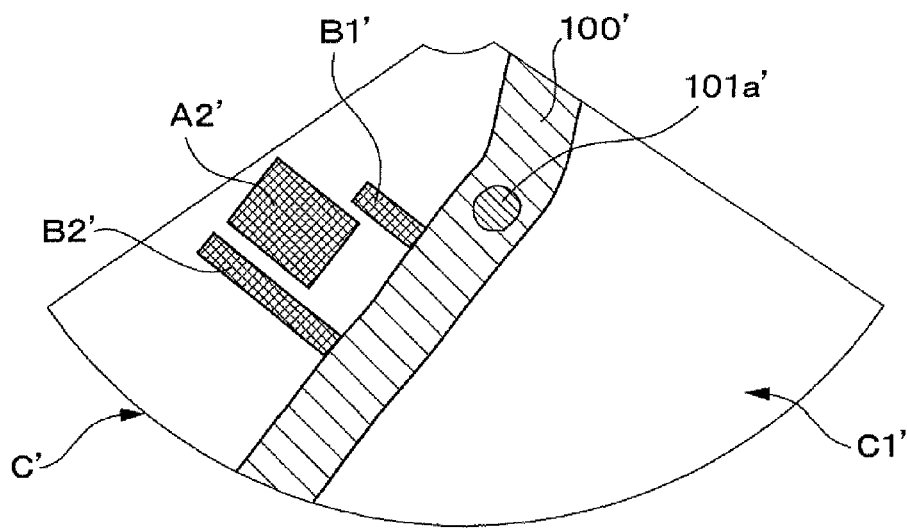
FIG. 11 shows an example of an ultrasound tomogram displayed on the display portion of the display apparatus after an insufflation operation is performed in the state in FIG. 9.

In this state, an insufflation operation is performed while the position of the puncture needle 17a being maintained. The insufflation operation is performed by the operator performing a predetermined operation of the control box 17b at hand to control the gas/drug supplier 17e. This operation causes gas (for example, carbon dioxide) to be supplied from the gas/drug supplier 17e through the hollow portion of the puncture needle 17a into the abdomen cavity. The abdomen cavity is filled with gas by the insufflation operation, which prevents transmitting and receiving ultrasound on the inside of the abdomen cavity. Thus, after the insufflation operation, an ultrasound tomogram cannot be visually observed in a region C1' inside the abdomen cavity in an ultrasound tomogram C' as shown in FIG. 11. Even in this case, the tomogram A2' of the second ultrasound scattering portion A2 on the puncture needle 17a, the tomograms B1' and B2' of the ultrasound scattering portions B1 and B2 on the flexible tube 15a, and the stomach wall 100 and the like can be observed, and thus the puncture position and the distal end position of the puncture needle 17a can be estimated and checked.

Figure 12:
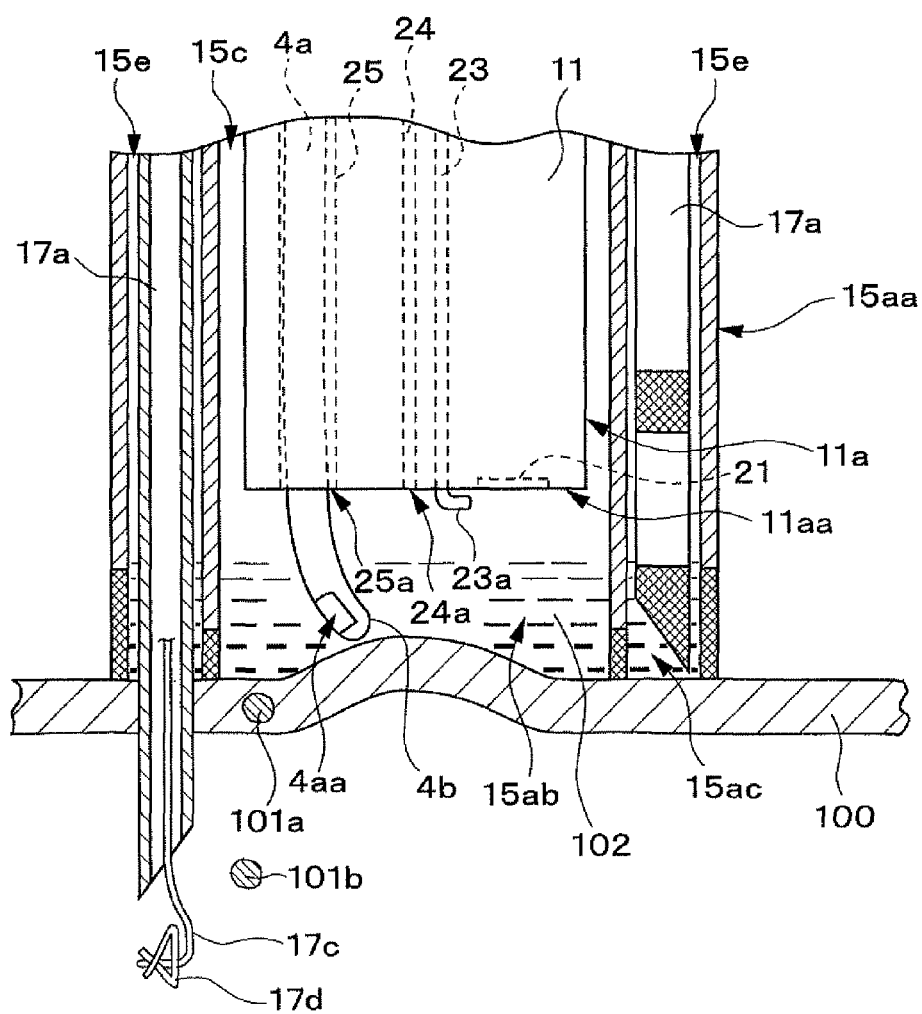
FIG. 12 shows a state where a suture treatment instrument is ejected from a distal end of the puncture needle in the state in FIG. 9.

Then, a driving operation of the T-bar 17d that is a suturing instrument and connected to the suture thread 17c is performed from the distal end of the puncture needle 17a inserted into the abdomen cavity and protruded. The driving operation of the suturing instrument is performed by the operator performing a predetermined operation of the control box 17b at hand. FIG. 12 shows a state where the T-bar 17d is ejected from the distal end of the puncture needle 17a.

Figure 13:
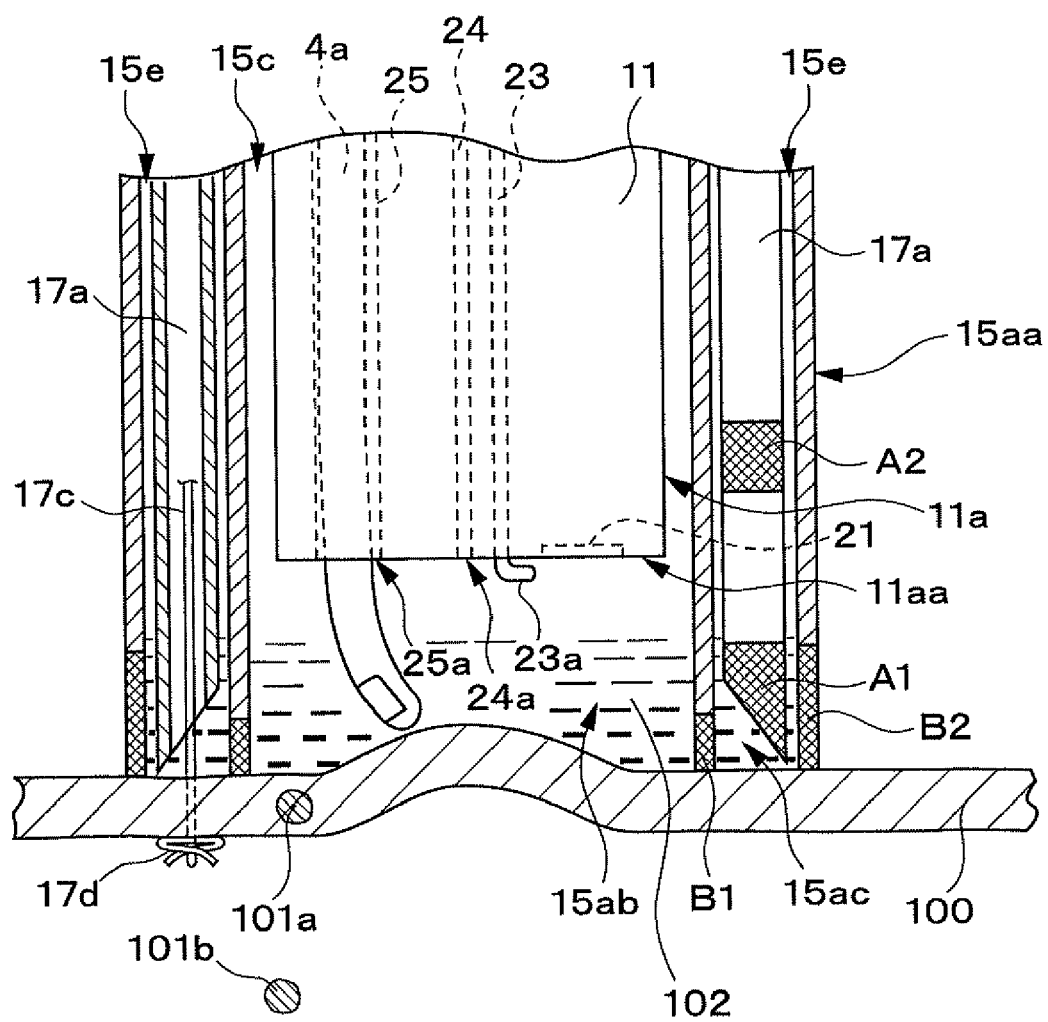
FIG. 13 shows a state where the puncture needle is drawn back from the state in FIG. 12 and housed in the flexible tube of the over tube.

After the T-bar 17d is ejected, the control box 17b is operated to return the puncture needle 17a into the treatment instrument insertion path 15e of the flexible tube 15a. Simultaneously, the suture thread 17c is drawn back. Thus, as shown in FIG. 13, the T-bar 17d is retained inside the abdomen cavity, and connected by the suture thread 17c through the stomach wall 100.

On the other hand, the puncture needle 17a is housed in the treatment instrument insertion path 15e of the flexible tube 15a of the over tube 15 inside the luminal organ. In this manner, the T-bar driving operation is finished.

When the T-bar 17d is driven a plurality of times, the over tube 15 or the endoscope 2 is rotated with respect to an insertion axis to set a positional relationship among the over tube 15, the ultrasound probe 4a, and the endoscope 2, and the driving operation as described above is repeated.

Then, surgery of an organ in an abdomen cavity (cholecystectomy in the present embodiment) by the NOTES procedure is performed by a predetermined process.

Specifically, first, the ultrasound probe 4a is removed from the treatment instrument channel 25 and the treatment instrument insertion opening 12e. Then, a perforating treatment instrument is inserted from the treatment instrument insertion opening 12e, and placed through the treatment instrument channel 25.

Under observation of endoscopic images by the endoscope 2, the perforating treatment instrument is used to make a dissection in a predetermined region on the stomach wall 10 by a predetermined operation, and the endoscope 2 is inserted into the abdomen cavity.

After the dissection is completed, the perforating treatment instrument is removed from the treatment instrument channel 25 and the treatment instrument insertion opening 12e.

Then, the endoscope 2 is inserted from the region dissected by the perforating treatment instrument into the abdomen cavity under observation of endoscopic images, and a desired region is observed. Simultaneously, a surgical treatment instrument is inserted from the treatment instrument insertion opening 12e, and placed through the treatment instrument channel 25.

Then, under observation of endoscopic images by the endoscope 2, surgery and treatment are performed using the surgical treatment instrument. In this state, not limited to the treatment using the surgical treatment instrument, but for example, the puncture needle 17a, the control box 17b and the gas/drug supplier 17e of the T-bar driver 17 may be used to supply a drug to a desired region in the abdomen cavity.

After the surgery and the treatment are completed, the endoscope 2 is removed from the dissected region and returned into the luminal organ. Also, various treatment instruments used are placed through the treatment instrument channel 25.

Then, the operation of the suture thread 17c by the control box 17b of the T-bar driver 17 is performed to perform the suture treatment of the dissected region.

After the suture treatment is completed, the operator operates the suction button 12c on the operation portion 12 of the endoscope 2 to release the suction operation. Then, the endoscope 2 and the over tube 15 are removed from the luminal organ. Thus, the whole procedure is finished.

As described above, according to the first embodiment, prior to the insufflation operation or the dissection operation performed in the suture treatment of the dissected region in surgery by the NOTES procedure, the puncture start position and the puncture direction of the puncture needle 17a of the suture treatment instrument (such as the T-bar driver 17) can be previously identified under observation of ultrasound tomograms. This can prevent unnecessary damage to organs in an abdomen cavity or blood vessels outside the luminal organ and allow the puncturing operation of the puncture needle 17a with safety and reliability. This also allows an efficient process of the NOTES procedure to reduce time for the whole procedure and easily reduce a burden on an operator or a subject.

In the treatment instrument system 1 according to the first embodiment, the flexible tube 15a bends by flexibility thereof according to a bending operation of the endoscope 2 placed through the over tube 15.

Figure 14:
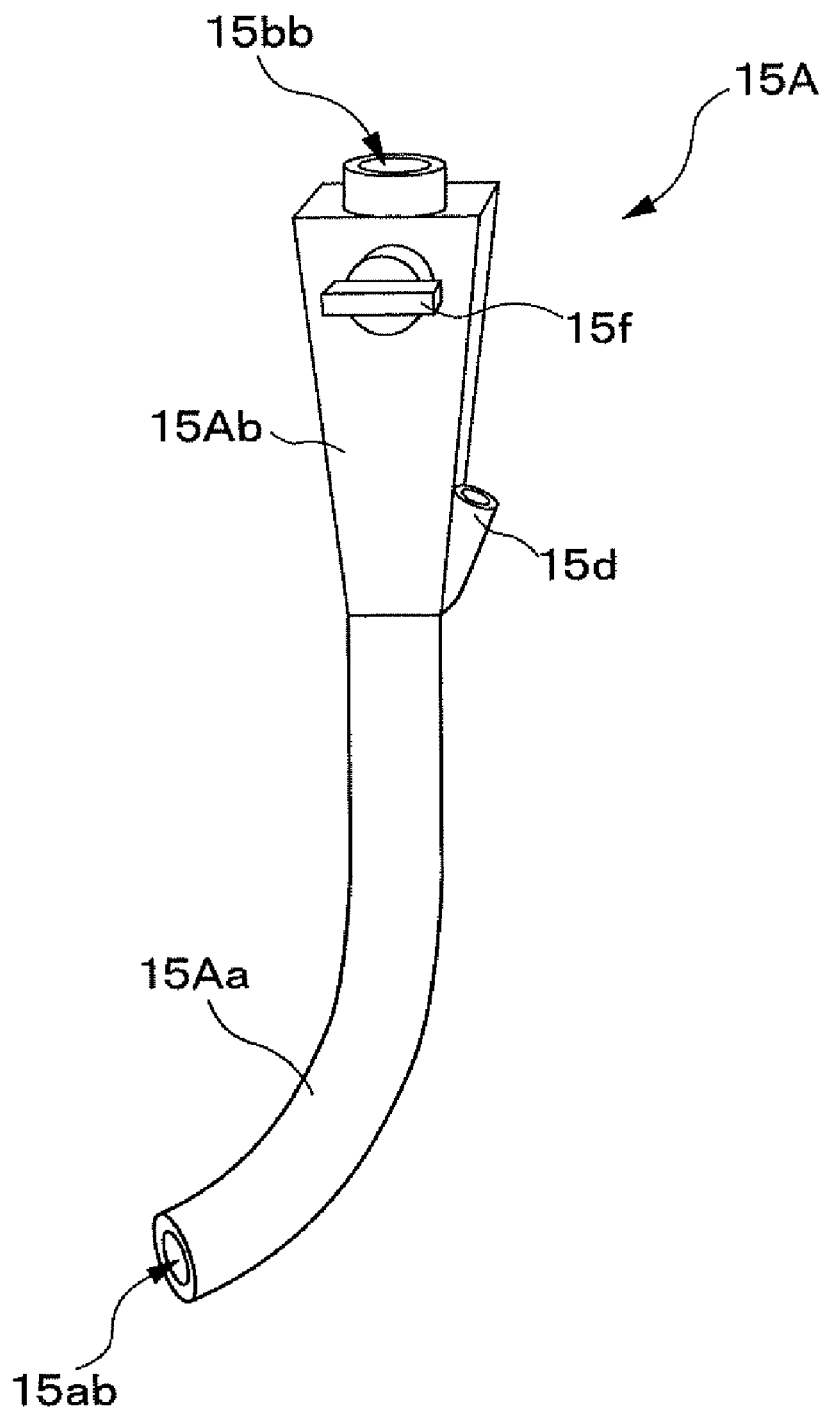
FIG. 14 is a schematic perspective view of a variant of the over tube in the treatment instrument system according to the first embodiment of the present invention.

Thus, it can be supposed that a mechanism for bending the distal end portion of the flexible tube is provided in the treatment instrument system itself. In this case, as shown in a variant in FIG. 14, a bending operation member 15f may be provided on a side surface of a proximal end forming portion 15Ab of an over tube 15A, which has substantially the same configuration as the over tube 15 (see FIG. 1) in the first embodiment, and a flexible tube 15Aa may have a bending mechanism as in a general endoscope.

With such a configuration, an operator can arbitrarily perform a bending operation of the over tube 15 itself, and thus can more easily perform an operation in insertion of the over tube 15 into a luminal organ in a body.

Next, a treatment instrument system according to a second embodiment of the present invention will be described with reference to FIGS. 15 to 17.

Figure 15:
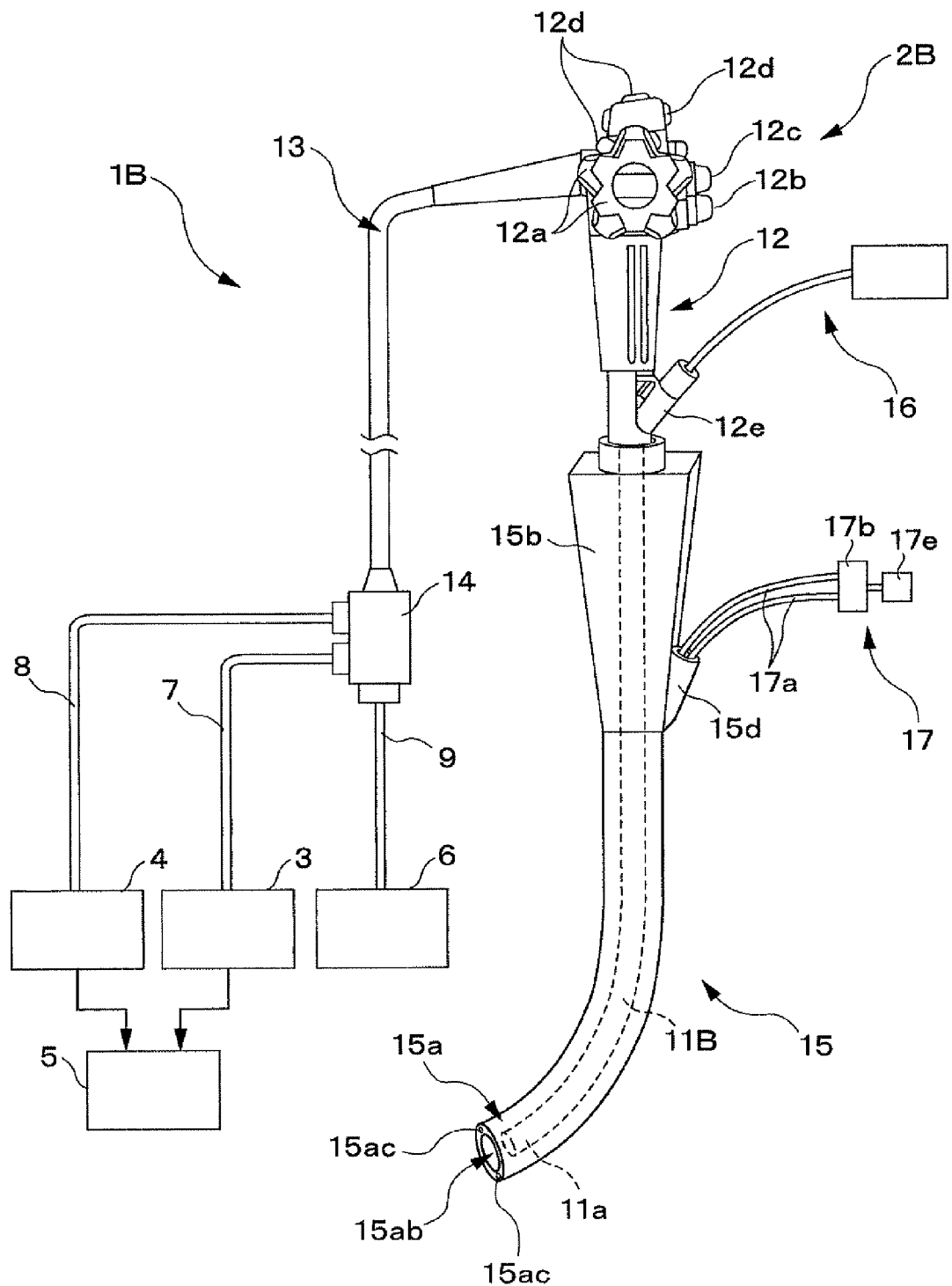
FIG. 15 is a schematic block diagram of an entire configuration of a treatment instrument system according to a second embodiment of the present invention.
Figure 16:
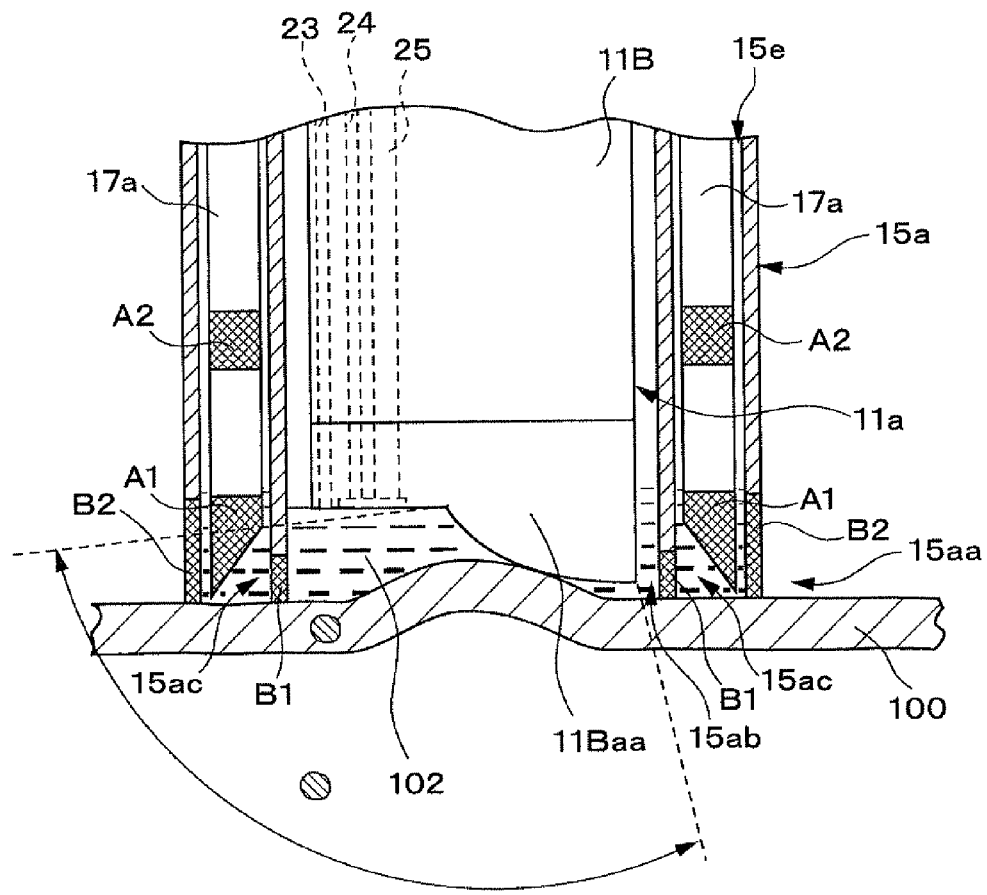
FIG. 16 is an enlarged cross-sectional view of essential portions in a state where distal end portions of an ultrasound endoscope and an over tube in an ultrasound endoscope apparatus in the treatment instrument system according to the present embodiment are cut along a surface in an insertion axis direction (a surface along the line [16]-[16] in FIG. 17)

FIG. 15 is a schematic block diagram of an entire configuration of the treatment instrument system according to the second embodiment of the present invention. FIG. 16 is an enlarged cross-sectional view of essential portions in a state where distal end portions of an ultrasound endoscope and an over tube in an ultrasound endoscope apparatus in the treatment instrument system according to the present embodiment are cut along a surface in an insertion axis direction (a surface along the line [16]-[16] in FIG. 17). FIG. 17 is a front view of distal end surfaces of the ultrasound endoscope and the over tube in FIG. 16.

In the first embodiment, the insertion portion 11 of the endoscope 2 is placed through the over tube 15, and the ultrasound probe 4a is inserted through the treatment instrument channel 25 of the endoscope 2. On the other hand, in the treatment instrument system according to the present embodiment, as shown in FIGS. 15 to 17, an insertion portion 11B of an ultrasound endoscope 2B is placed through an over tube 15.

A schematic configuration of an ultrasound endoscope apparatus including the ultrasound endoscope 2B in the present embodiment will be now described.

As shown in FIG. 15, the ultrasound endoscope apparatus used in the treatment instrument system 1 mainly includes an ultrasound endoscope 2B, an endoscope observing apparatus 3, an ultrasound observing apparatus 4, a display apparatus 5, a light source device 6, a video cable 7, an ultrasound cable 8, and a light source cable 9.

The ultrasound endoscope apparatus in FIG. 15 is different from the endoscope apparatus in the first embodiment in including the ultrasound endoscope 2B in place of the endoscope 2 (see FIG. 1 or the like) in the endoscope apparatus in the first embodiment, and including components suitable for ultrasound observation such as the ultrasound observing apparatus 4 and the ultrasound cable 8 in connection with use of the ultrasound endoscope 2B.

Specifically, an ultrasound observing function performed by the ultrasound probe 4a inserted from the treatment instrument insertion opening 12e for use, the ultrasound observing apparatus 4 connected to the ultrasound probe 4a, the display apparatus 5a, and the like in the endoscope apparatus in the first embodiment is performed by the ultrasound endoscope 2B placed through the over tube 15 and the ultrasound observing apparatus 4 connected to the ultrasound endoscope 2B in the present embodiment.

The ultrasound endoscope 2B applied to the treatment instrument system 1B according to the present embodiment is a general ultrasound endoscope having the same endoscopic image observing function as that of the endoscope 2 in the first embodiment and also having an ultrasound observing function, and is, for example, a forward viewing convex type ultrasound endoscope.

The ultrasound endoscope 2B includes a basic configuration (the endoscopic image observing function) of the endoscope 2 in the first embodiment, and further includes an ultrasound unit 11Baa for achieving the ultrasound observing function in a distal end rigid portion 11a of an insertion portion 11B. Through the insertion portion 11B, an operation portion 12, a universal cord 13, and a connector portion 14, signal lines are placed for transmitting various control signals or ultrasound signals between the ultrasound unit 11Baa and the ultrasound observing apparatus 4.

Other configurations are the same as in the first embodiment.

A process of surgery of an organ in an abdomen cavity, for example, cholecystectomy by the NOTES procedure using the treatment instrument system 1B thus configured according to the present embodiment is substantially the same as in the first embodiment. An outline of the process of the procedure by the present embodiment will be now described. Detailed descriptions on the process of the procedure as in the first embodiment will be omitted, and a different process will be described.

First, as shown in FIG. 15, the ultrasound endoscope 2B is placed through the over tube 15. The placing operation is the same as that in placing the endoscope 2 through the over tube 15 in the first embodiment.

In the state in FIG. 15, that is, in the state where the ultrasound endoscope 2B is placed through the over tube 15, a flexible tube 15a is inserted through a natural orifice (for example, an oral cavity) of a subject (patient) into a target luminal organ (for example, a stomach) under observation of endoscopic images. This insertion operation is the same as that in the first embodiment.

Then, when the flexible tube 15a of the over tube 15 is inserted into the luminal organ and a distal end surface 15aa of the flexible tube 15a abuts against a stomach wall 100, in this state, an operator performs a suction operation as in the first embodiment under observation of endoscopic images and performs a water feeding operation. Thus, the state of a distal end portion of the over tube 15 becomes as shown in FIG. 16.

Then, the operator changes a position of the ultrasound unit 11Baa of the ultrasound endoscope 2B relative to the over tube 15 to a position around an insertion axis of the flexible tube 15a while observing endoscopic images and ultrasound tomograms so that ultrasound scattering portions B1 and B2 on the over tube 15 are simultaneously displayed on a display portion of a display apparatus 5a (refer to the description with reference to FIG. 8 in the first embodiment).

The operator searches and identifies a puncture position of a puncture needle 17a while observing the ultrasound tomograms (displayed on the display apparatus 5a) by the ultrasound endoscope 2B and the endoscopic images (displayed on the display apparatus 5) by the endoscope 2. The operator also checks an organ in an abdomen cavity or a running state of blood vessels in the abdomen cavity. The process of searching and identifying the puncture position and the process of checking an organ in an abdomen cavity or a running state of blood vessels are the same as in the first embodiment.

Next, a puncturing operation of the puncture needle 17a is performed under ultrasound observation. The process of the puncturing operation and the process of deciding a puncture depth of the puncture needle 17a prior to the puncturing operation are also the same as that in the first embodiment.

The puncturing operation of the puncture needle 17a is performed, then an insufflation operation is performed, and a driving operation of a T-bar 17d (not shown in FIG. 15; see FIG. 12) is performed. The driving operation of the T-bar is also the same as in the first embodiment.

Then, surgery of an organ in an abdomen cavity (for example, cholecystectomy) by the NOTES procedure is performed by a predetermined process (as in the first embodiment). After the procedure is finished, a dissected region is sutured, then a suction state is released by an air feeding operation, and the over tube 15 through which the ultrasound endoscope 2B is placed is removed from the luminal organ. Thus, the whole procedure is finished.

As described above, also in the treatment instrument system 1B of the second embodiment, substantially the same advantages as the first embodiment can be obtained.

In the second embodiment, the ultrasound endoscope apparatus is used to allow ultrasound tomograms with high definition over a wider range to be obtained as compared with the system according to the first embodiment using the ultrasound probe 4a. The puncturing operation of the puncture needle 17a of the suture treatment instrument (such as the T-bar driver 17) can be performed under observation of the ultrasound tomograms with high definition over a wider range, thereby contributing to an increase in safety of the puncturing operation in the present embodiment.

Thus, in the first and the second embodiment, by the ultrasound observing function of the ultrasound probe 4a or the ultrasound endoscope 2B, the treatment instrument system can be effectively used as means for checking the position of an organ in the abdomen cavity or the running state of blood vessels outside the luminal organ through which the treatment instrument is inserted, and the ultrasound scattering portions A1, A2, B1 and B2 are provided in predetermined regions on the suture treatment instrument (such as the T-bar driver 17) and the distal end of the flexible tube 15a of the over tube 15. Thus, the ultrasound scattering portions can be easily checked under observation of ultrasound tomograms displayed on the display portion using the ultrasound probe 4a and the ultrasound endoscope 2B, which may serve as effective means for identifying, setting, and checking a puncture start position, a puncture direction, and a puncture depth of the puncture needle 17a for performing, for example, insufflation relative to a wall surface of a luminal organ (such as a stomach).

Figure 17:
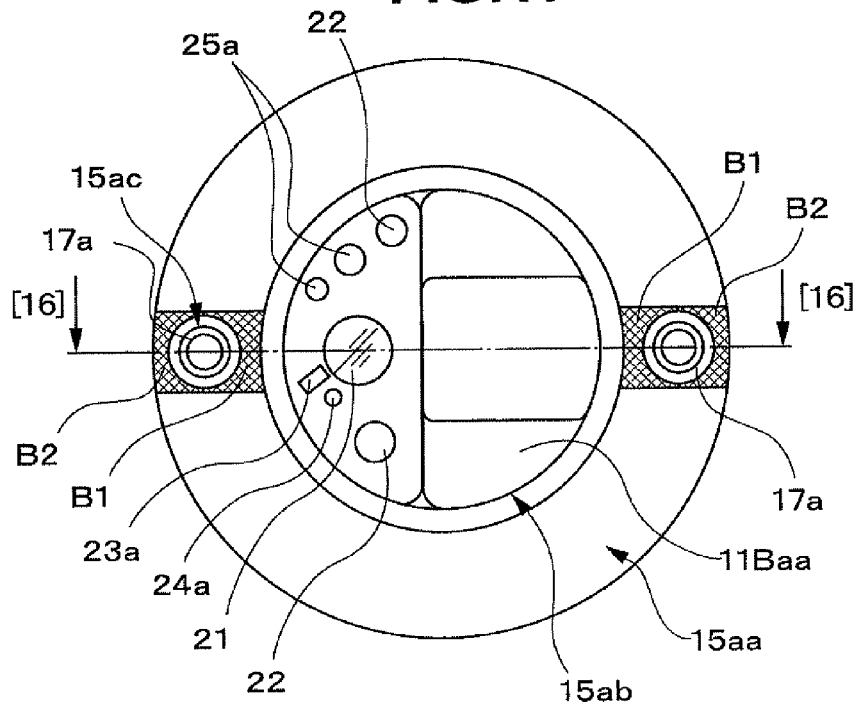
FIG. 17 is a front view of distal end surfaces of the ultrasound endoscope and the over tube of the present embodiment.

In the first and second embodiments, the example in which the two treatment instrument insertion paths 15e and the two treatment instrument insertion opening 15ac are formed in the over tube 15 is shown as in FIGS. 3 and 17. However, at least one treatment instrument insertion path 15e and at least one treatment instrument insertion opening 15ac may be provided, and the numbers thereof may be two as in the above described embodiments, or may be three or more. When a plurality of treatment instrument insertion paths 15e are provided, the treatment instrument insertion paths 15e are desirably arranged so that treatment instrument insertion openings 15ac are arranged at circumferentially regular intervals when viewed from the front of the distal end surface of the over tube 15.

Figure 18:
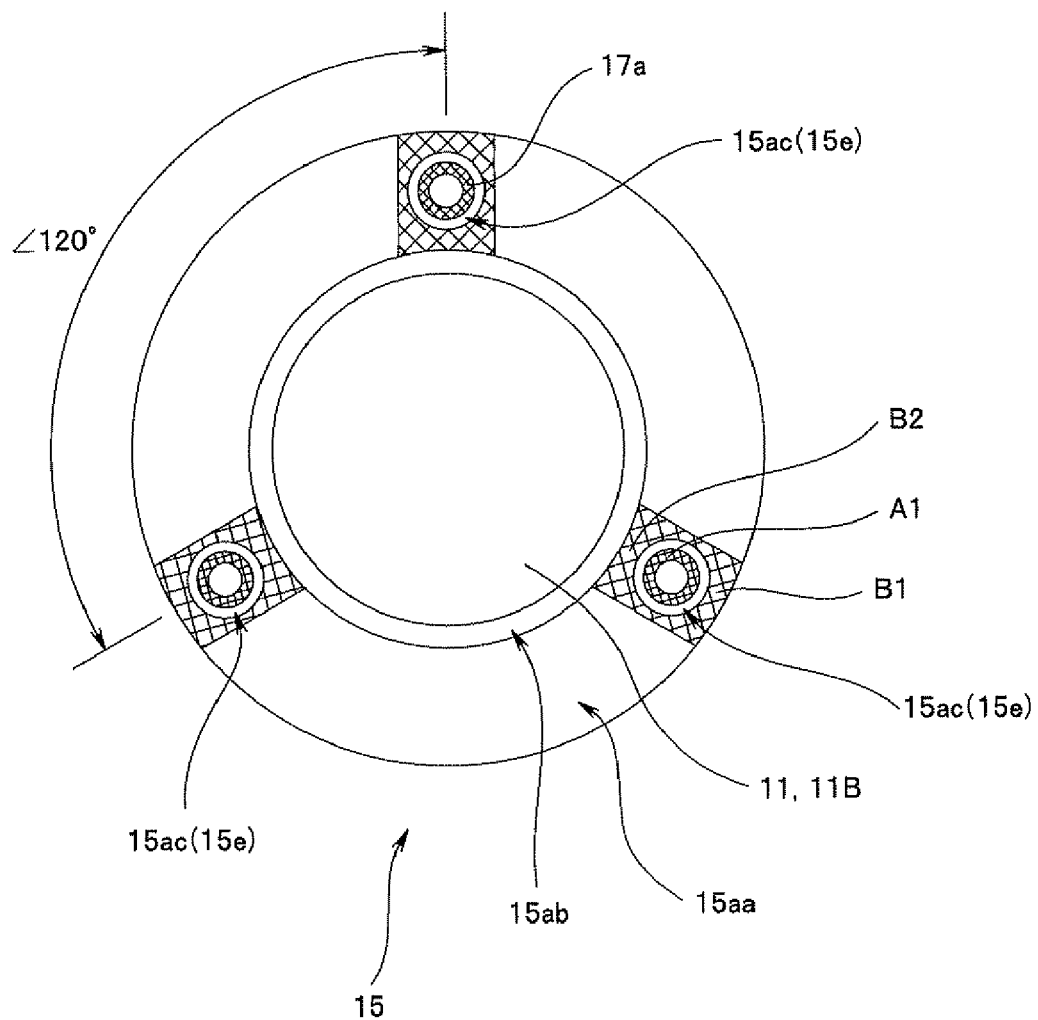
FIG. 18 is a front view of a distal end surface of an over tube in an arrangement example in which three treatment instrument insertion paths are provided in the over tube in the treatment instrument system according to the present invention.

For example, when three treatment instrument insertion paths 15e are provided, as shown in FIG. 18, the treatment instrument insertion paths 15e are arranged at 120° intervals so that treatment instrument insertion openings 15ac are arranged at regular intervals circumferentially of the over tube 15 when viewed from the front of the distal end surface of the over tube 15.

Figure 19:
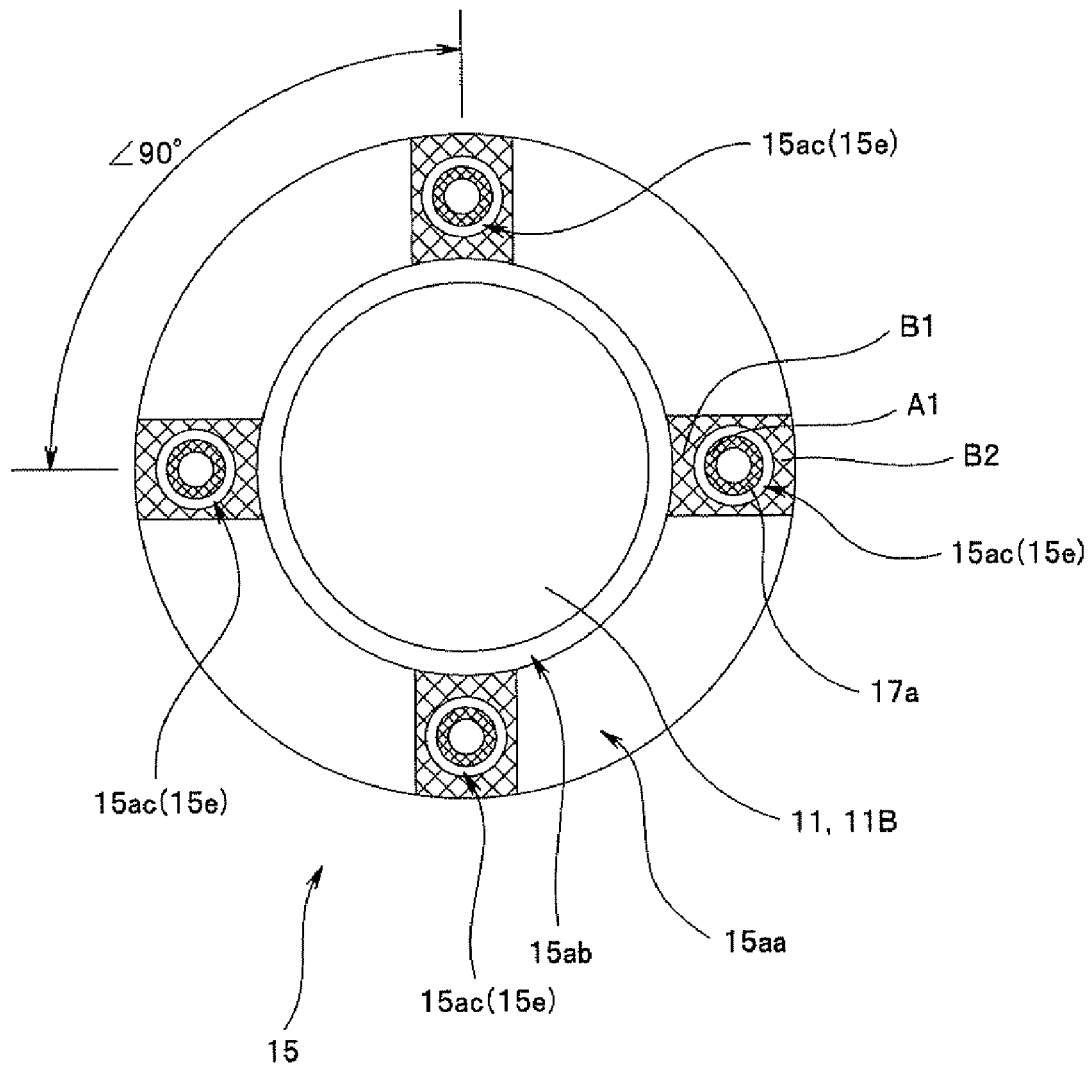
FIG. 19 is a front view of a distal end surface of an over tube in an arrangement example in which four treatment instrument insertion paths are provided in the over tube in the treatment instrument system according to the present invention.

Similarly, when four treatment instrument insertion paths 15e are provided, as shown in FIG. 19, the treatment instrument insertion paths 15e are arranged at 90° intervals so that treatment instrument insertion openings 15ac are arranged at regular intervals circumferentially of the over tube 15 when viewed from the front of the distal end surface of the over tube 15.

In both of the arrangements in FIGS. 18 and 19, ultrasound scattering portions B1 and B2 are provided at a peripheral edge of each treatment instrument insertion opening 15ac in the over tube 15.

In the first and second embodiments, the ultrasound scattering portions A1 and A2 provided at the distal end portion of the puncture needle 17a and the ultrasound scattering portions B1 and B2 provided at the distal end portion (the peripheral edge of the treatment instrument insertion opening 15ac) in the over tube 15 are formed at an area entirely around the peripheral edge of each of the distal end portion of the puncture needle 17a and the treatment instrument insertion opening 15ac when viewed from the front of the distal end surface of the over tube 15 (see FIGS. 3, 17, 18 and 19). However, the arrangement of the ultrasound scattering portions is not limited to the above described example, and various arrangement forms may be supposed.

In this case, an ultrasound scattering portion placed inside needs to be placed so as not to obstruct an ultrasound scattering portion placed outside. Specifically, the ultrasound scattering portions are arranged so that ultrasound transmitted from the ultrasound units (4aa and 11Baa) placed in the endoscope insertion path 15c of the over tube 15 reliably reaches all the ultrasound scattering portions formed.

Figure 20:
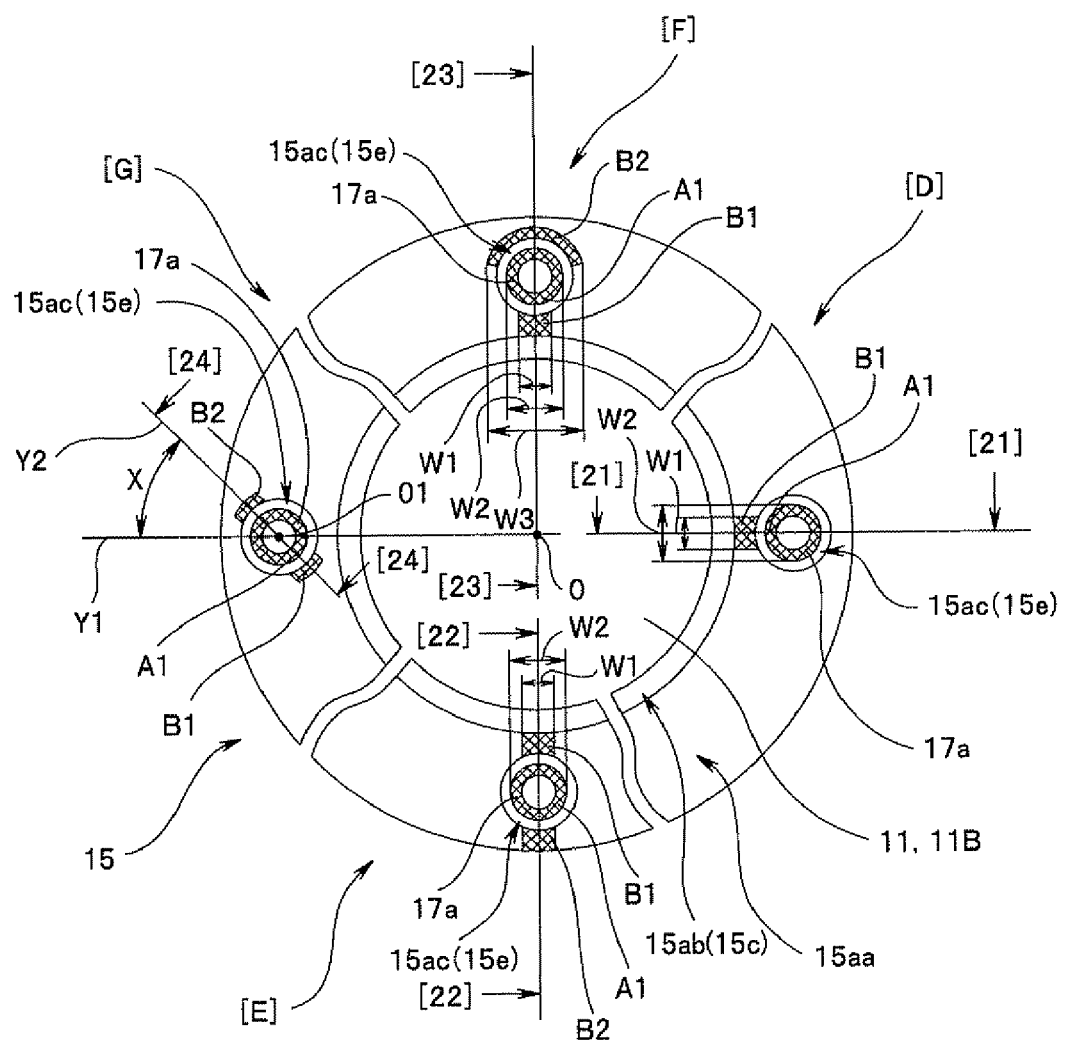
FIG. 20 is a front view of a distal end surface of an over tube in an arrangement example of ultrasound scattering portions provided at the distal end portion of the over tube in the treatment instrument system according to the present invention.

Thus, for example, as in a section denoted by reference numeral [D] in FIG. 20, the ultrasound scattering portion B1 may be provided in an area that is a part of the peripheral edge of the treatment instrument insertion opening 15ac in the over tube 15 and closer to the inner side (closer to the endoscope insertion path 15c), and the ultrasound scattering portions A1 and A2 may be provided at an area entirely around the peripheral edge of the puncture needle 17a. In this case, a width W1 of the ultrasound scattering portion B1 is set to be smaller than a width W2 of the ultrasound scattering portion A1 and A2, that is, a diameter W of an outer circumference of the puncture needle 17a.

In the arrangement form in the example, a part of the ultrasound scattering portion A1 is obstructed by the ultrasound scattering portion B1. Thus, as in a cross-sectional view in FIG. 21, a longitudinal size H2 from the distal end surface 15aa of the ultrasound scattering portion A1 is set to be larger than a longitudinal size H1 from the distal end surface 15aa of the over tube 15. Thus, all the ultrasound scattering portions A1, A2, B1 and B2 can be reliably checked with an ultrasound tomogram.

In the first and second embodiments, the ultrasound scattering portion is provided at the area entirely around the peripheral edge of the treatment instrument insertion opening 15ac in the over tube 15, and as shown in FIG. 2, the longitudinal size L1 (in the insertion direction) of the inner area B1 of the ultrasound scattering portion is set to be smaller than the longitudinal size L2 of the outer area B2. Thus, two tomograms B1' and B2' corresponding to the ultrasound scattering portions B1 and B2 are displayed on the ultrasound tomogram as shown in FIG. 8. In this case, a direction substantially perpendicular to an arranging direction of the two tomograms B1' and B2' can be advantageously easily checked as an advancing direction of the puncture needle 17a.

Figure 21:
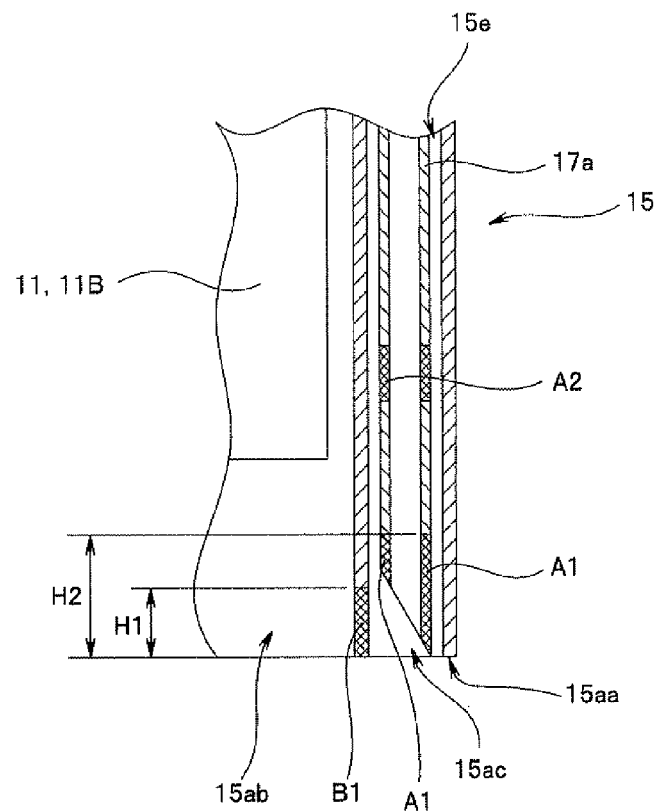
FIG. 21 is a cross-sectional view taken along the line [21]-[21] in FIG. 20.

On the other hand, in the arrangement form in the section [D] in FIG. 20 and FIG. 21, only the inner area B1 of the ultrasound scattering portion is provided on the over tube 15, and an advancing direction of the puncture needle 17a cannot be estimated in a state where only the ultrasound scattering portion B1 is displayed. In this case, the puncture needle 17a is inserted to cause the ultrasound scattering portion A1 to be displayed simultaneously with the ultrasound scattering portion B1, and thus the advancing direction of the puncture needle 17a can be checked by observing a relative positional relationship between the ultrasound scattering portions B1 and A1.

Also, as in a section denoted by reference numeral [E] in FIG. 20, the ultrasound scattering portions B1 and B2 may be provided in an area that is the part of the peripheral edge of the treatment instrument insertion opening 15ac in the over tube 15 and closer to the inner side (closer to the endoscope insertion path 15c) and an area closer to the outer periphery. The ultrasound scattering portion A1 on the puncture needle 17a is also provided at an area entirely around the peripheral edge. In this case, the relationship between the width W1 of the ultrasound scattering portions B1 and B2 and the width W2 of the ultrasound scattering portion A1 is set so that a relationship of W1<W2 is satisfied.

Figure 22:
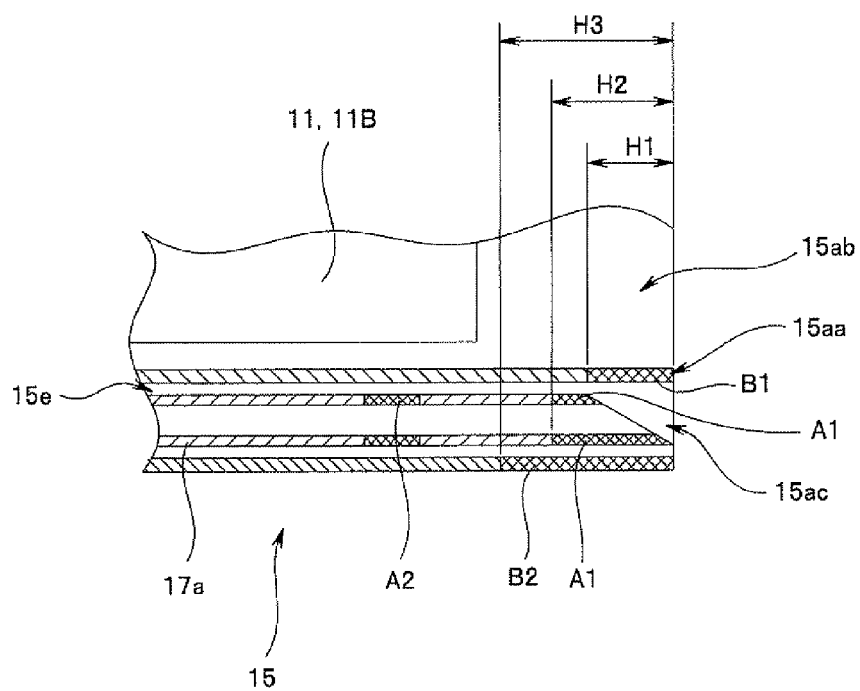
FIG. 22 is a cross-sectional view taken along the line [22]-[22] in FIG. 20.

In the arrangement form in the example, as in the example in FIG. 21, a part of the ultrasound scattering portions A1 and B2 is obstructed by the ultrasound scattering portion B1. Thus, in the example, as in a cross-sectional view in FIG. 22, a longitudinal size H1 from the distal end surface 15aa of the over tube 15, a longitudinal size H2 from the distal end surface 15aa of the ultrasound scattering portion A1, and a longitudinal size H3 from the distal end surface 15aa of the ultrasound scattering portion 132 are set so that the sizes become larger from the inner side toward the outer side, that is, a relationship of H1<H2<H3 is satisfied. Thus, all the ultrasound scattering portions A1, A2, B1 and B2 can be reliably checked with the ultrasound tomogram.

In the arrangement form in a section denoted by reference numeral [F] in FIG. 20, similarly to the arrangement form in the section [E], the ultrasound scattering portions B1 and B2 are provided on the inner side and the outer peripheral side at the peripheral edge of the treatment instrument insertion opening 15ac in the over tube 15, and the ultrasound scattering portion A1 on the puncture needle 17a is also provided entirely around the peripheral edge thereof. In the example, a width W1 of the ultrasound scattering portion B1, a width W2 of the ultrasound scattering portion A1, and a width W3 of the ultrasound scattering portion B2 are set so that the widths become larger from the inner side toward the outer side, that is, a relationship of W1<W2<W3 is satisfied.

Figure 23:
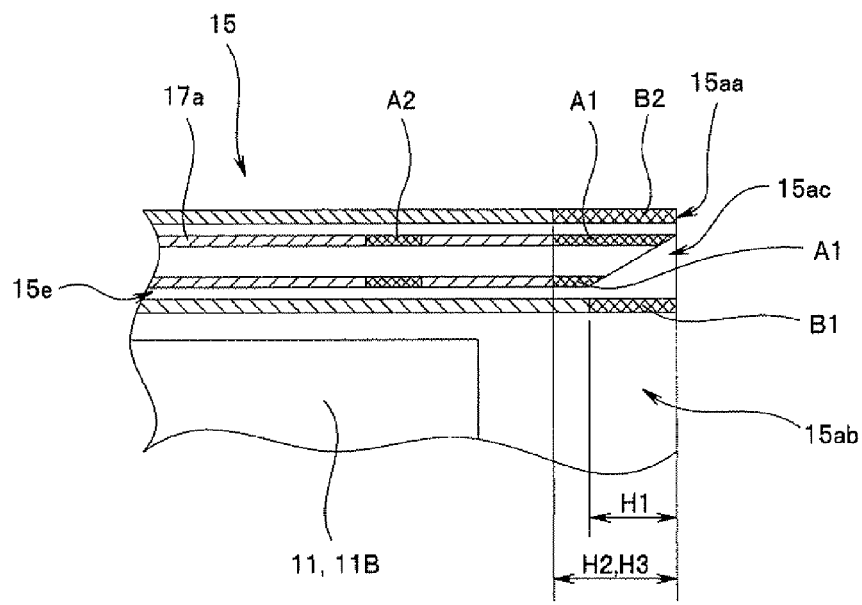
FIG. 23 is a cross-sectional view taken along the line [23]-[23] in FIG. 20.

In the arrangement form in the example, the part of the ultrasound scattering portions A1 and B2 is obstructed by the ultrasound scattering portion B1 as in the example in FIG. 21, but the ultrasound scattering portions have the different widths as described above. Thus, in the example, as in a cross-sectional view in FIG. 23, even if the relationship between the longitudinal size H1 from the distal end surface 15aa of the over tube 15, the longitudinal size H2 from the distal end surface 15aa of the ultrasound scattering portion A1, and the longitudinal size H3 from the distal end surface 15aa of the ultrasound scattering portion B2 is H1<H2=H3, all the ultrasound scattering portions A1, A2, B1 and B2 can be reliably checked with the ultrasound tomogram.

Further, the ultrasound scattering portions B1 and B2 on the over tube 15 may be in the arrangement form denoted by reference numeral [G] in FIG. 20.

In the arrangement example, the ultrasound scattering portions B1 and B2 are arranged so as to be opposed to each other on two areas at a peripheral edge of the treatment instrument insertion opening 15ac and on a line Y2 including a center point O1 and having a predetermined angle X with respect to a line Y1 including a center point O when the distal end surface of the over tube 15 is viewed from the front and the center point O1 when the treatment instrument insertion opening 15ac in the over tube 15 is viewed from the front.

Figure 24:
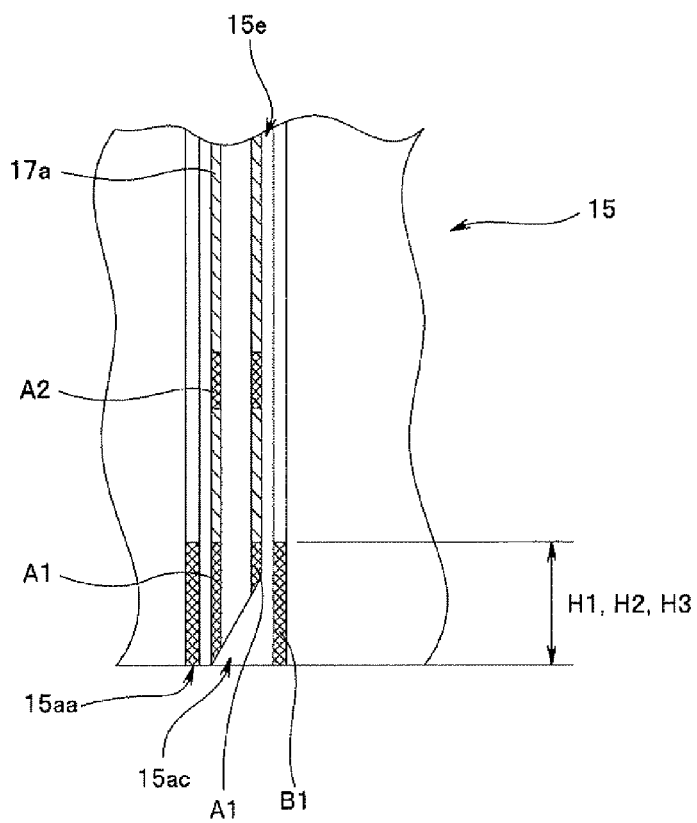
FIG. 24 is a cross-sectional view taken along the line [24]-[24] in FIG. 20.

In this case, as shown in a cross-sectional view in FIG. 24, even if the relationship among the longitudinal size H1 from the distal end surface 15aa of the over tube 15, the longitudinal size H2 from the distal end surface 15aa of the ultrasound scattering portion A1, and the longitudinal size H3 from the distal end surface 15aa of the ultrasound scattering portion B2 is H1=H2=H3, all the ultrasound scattering portions A1, A2, B1 and B2 can be reliably checked on the ultrasound tomogram.

Through the treatment instrument insertion path provided in the over tube applied to the treatment instrument system according to the present invention, treatment instruments other than the puncture needle of the suture treatment instrument can be inserted as disclosed in the above described embodiments and the examples in FIGS. 18 to 24.

Thus, a further plurality of treatment instrument insertion paths and treatment instrument insertion openings may be formed in the over tube. Achieving such a configuration allows, for example, various types of treatment instruments to be inserted through the plurality of insertion paths, respectively, and the various types of treatment instruments can be simultaneously used, thereby contributing to an improvement in operability. Also, the various types of treatment instruments can be simultaneously placed through the over tube, thereby reducing trouble or frequency of replacement of the treatment instruments and allowing a more effective procedure.

Various examples of arrangement forms in providing a plurality of treatment instrument insertion openings in the over tube will be now described.

Figure 25:
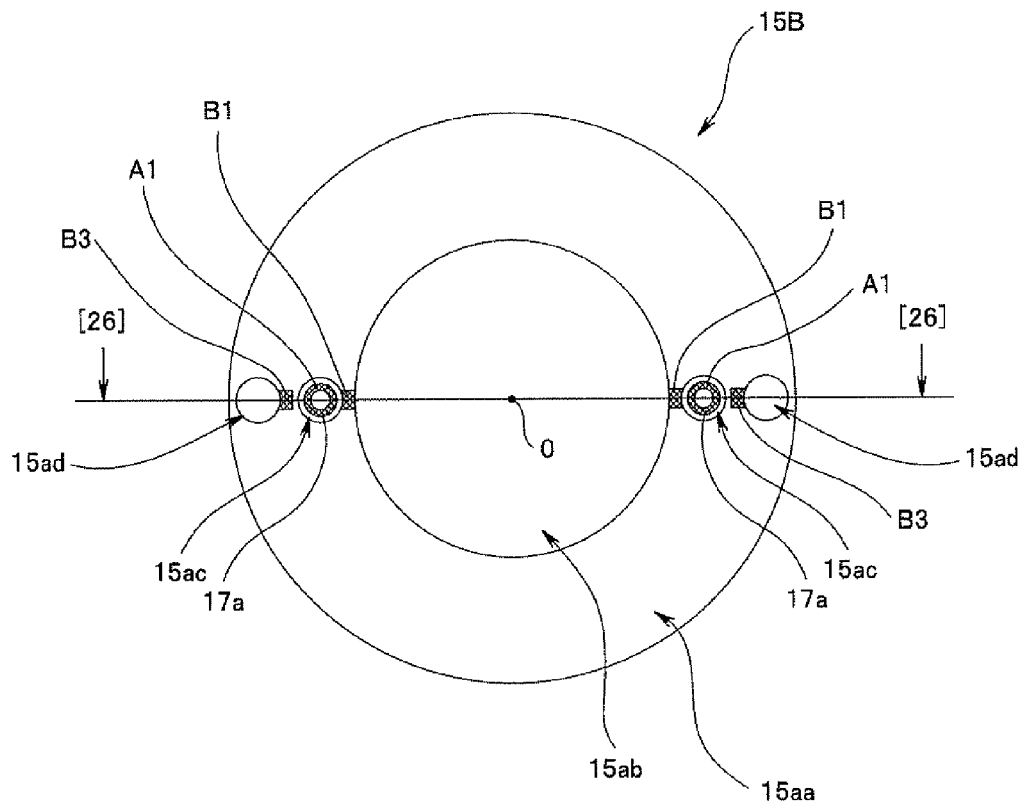
FIG. 25 is a front view of a distal end surface of an over tube in a first arrangement form in providing a plurality of treatment instrument insertion openings in the treatment instrument system according to the present invention.
Figure 26:
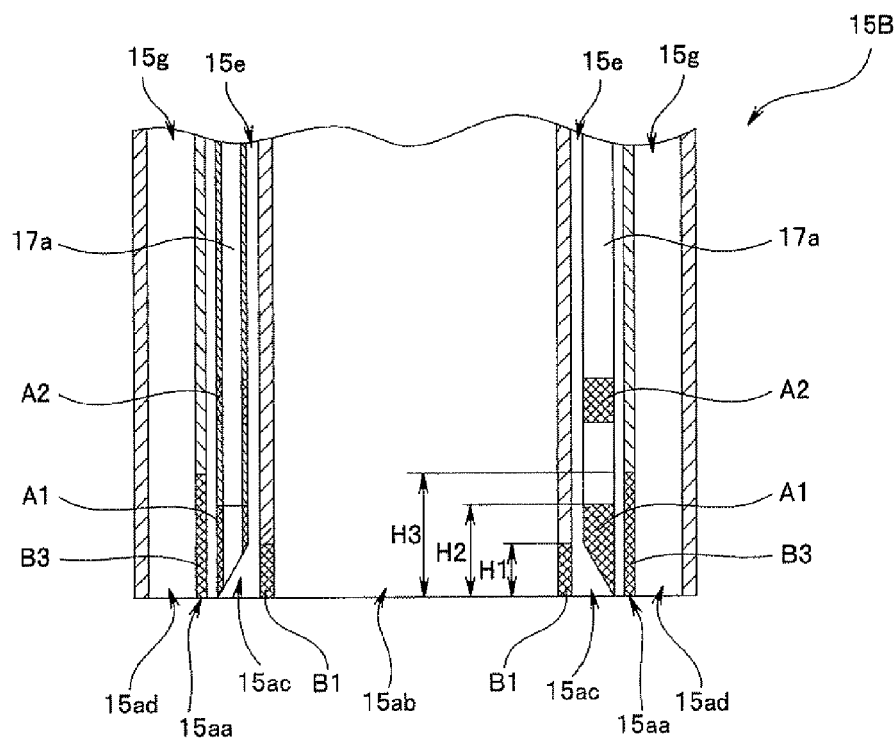
FIG. 26 is a cross-sectional view taken along the line [26]-[26] in FIG. 25.

First, FIG. 25 is a front view of a distal end surface 15aa of an over tube 15B in a first arrangement form of a plurality of treatment instrument insertion openings in the treatment instrument system according to the present invention. FIG. 26 is a cross-sectional view taken along the line [26]-[26] in FIG. 25.

As shown in FIG. 25, in the first arrangement form, treatment instrument insertion openings 15ac and 15ad are radially arranged with respect to a center point O of the over tube 15B.

An ultrasound scattering portion B1 is provided in a part of an area on an inner side at a peripheral edge of the treatment instrument insertion opening 15ac positioned closer to a center point O, and an ultrasound scattering portion B3 is provided in a part of an area on an inner side at a peripheral edge of the treatment instrument insertion opening 15ad positioned apart from the center point O. On a distal end portion of the puncture needle 17a, ultrasound scattering portions A1 and A2 are each provided in a predetermined range entirely around an outer peripheral surface.

In the arrangement form, for checking all the ultrasound scattering portions A1, A2, B1 and B2 on the ultrasound tomogram without problems, as shown in a cross-sectional view in FIG. 26, a relationship between a longitudinal size H1 from a distal end surface 15aa of the over tube 15, a longitudinal size H2 from a distal end surface 15aa of the ultrasound scattering portion A1, and a longitudinal size H3 from a distal end surface 15aa of the ultrasound scattering portion B3 is H1<H2<H3.

Figure 27:
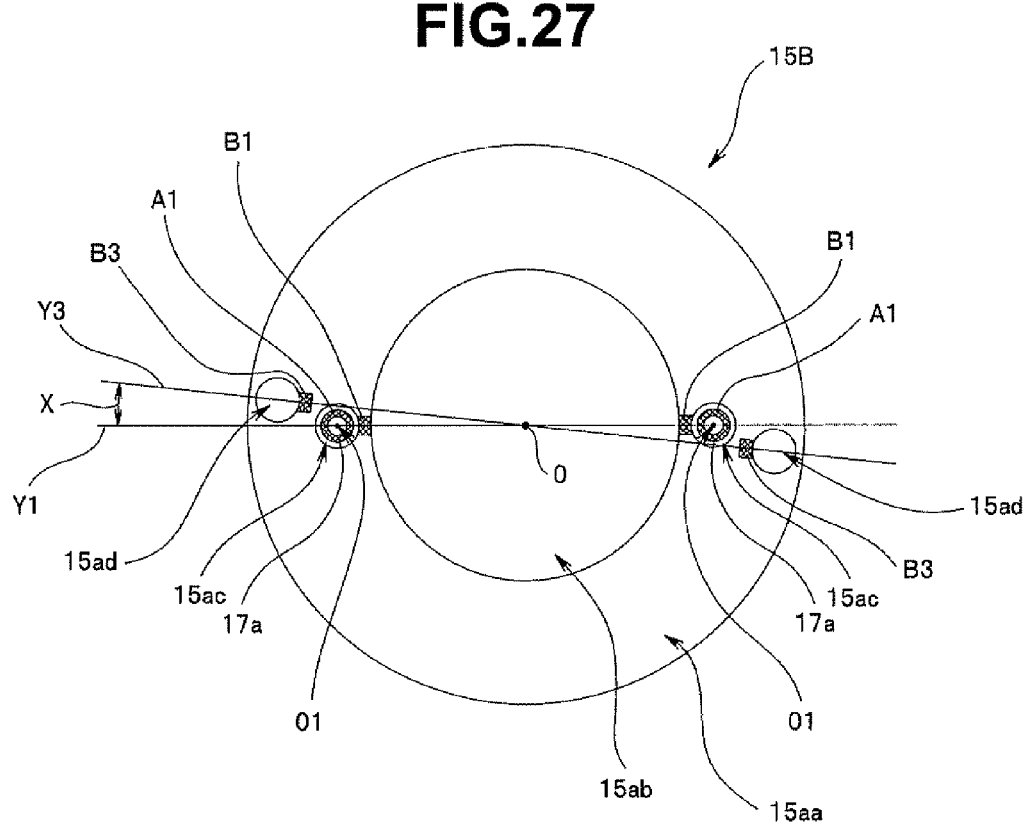
FIG. 27 is a front view of a distal end surface of an over tube in a second arrangement form in providing a plurality of treatment instrument insertion openings in the treatment instrument system according to the present invention.

Next, FIG. 27 is a front view of a distal end surface 15aa of an over tube 15B showing a second arrangement form of a plurality of treatment instrument insertion openings in the treatment instrument system according to the present invention.

As shown in FIG. 27, the second arrangement form is substantially the same as the first arrangement form, and different in that from the pair of treatment instrument insertion openings 15ac placed inside with respect to the center point O and opposed to each other in the first arrangement form, a pair of treatment instrument insertion openings 15ad placed outside the pair of treatment instrument insertion openings 15ac and opposite to each other are displaced.

In the example in FIG. 27, the pair of treatment instrument insertion openings 15ad are positioned on a line Y3 rotated by a predetermined angle of X° around the center point O with respect to the line Y1 including center points of the pair of treatment instrument insertion openings 15ac.

In the arrangement form, a longitudinal size H1 from a distal end surface 15aa of an over tube 15 may be equal to a longitudinal size H3 from a distal end surface 15aa of an ultrasound scattering portion B3 (H1=H3). If a relationship between the sizes H1 and H3 and a longitudinal size H2 from a distal end surface 15aa of a ultrasound scattering portion A1 is set to be H1, H3<H2, all the ultrasound scattering portions A1, A2, B1 and B2 can be checked with an ultrasound tomogram without problems.

Figure 28:
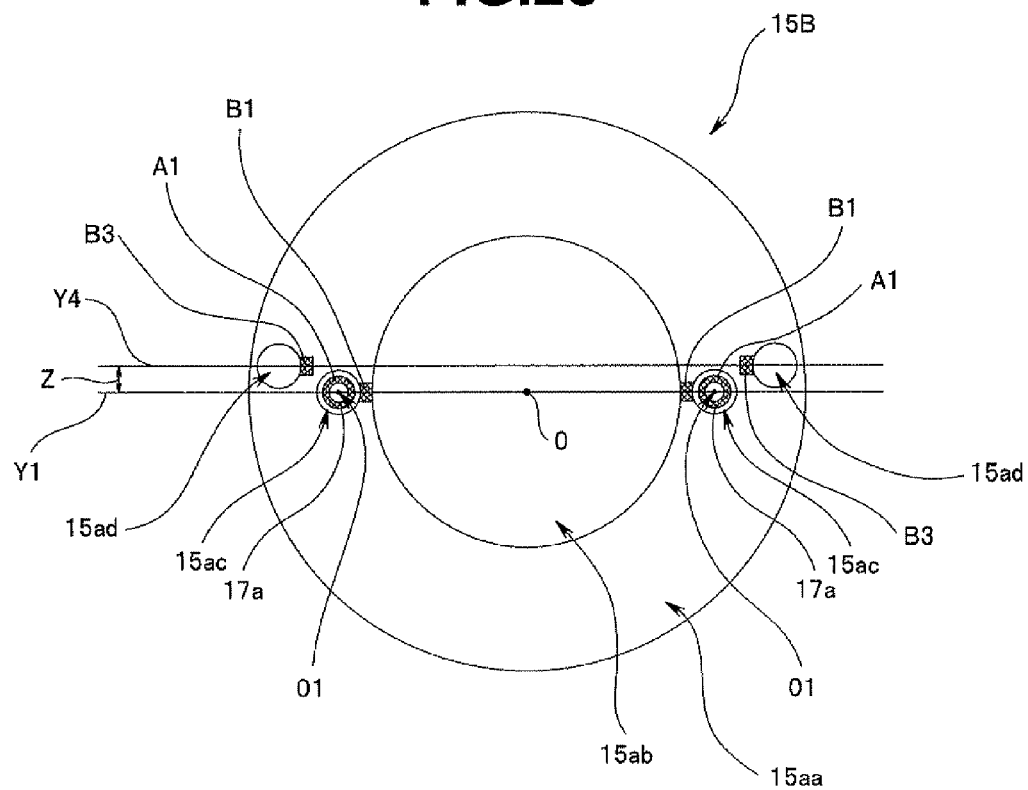
FIG. 28 is a front view of a distal end surface of an over tube in a third arrangement form in providing a plurality of treatment instrument insertion openings in the treatment instrument system according to the present invention.

In the example in FIG. 27, from one treatment instrument insertion opening, the other treatment instrument insertion opening is displaced in the rotational direction, but not limited thereto. For example, as shown in a third arrangement form in FIG. 28, a pair of treatment instrument insertion openings 15ad may be positioned on a line Y4 placed at a predetermined distance Z in parallel with the line Y1 including the center point O1 of the pair of treatment instrument insertion openings 15ac.

When the plurality of treatment instrument insertion openings are arranged as in FIGS. 25 to 27, for example, a treatment instrument (such as a suture treatment instrument 17) for driving a puncture needle into tissue in a body cavity, or the like is desirably inserted through the treatment instrument insertion opening 15ac (treatment instrument insertion path 15B placed closer to the center point O (inner side) of the over tube 15B.

Various arrangement forms of the ultrasound scattering portions provided at the distal end portion of the over tube are supposed such as the ultrasound scattering portions being provided in the area entirely around the peripheral edge or provided in the part of the predetermined area at the peripheral edge as disclosed in the above described embodiments and the examples in FIGS. 18 to 27. For the longitudinal range (in the insertion direction) of the ultrasound scattering portion on the over tube, the size from the distal end surface of the over tube is set in consideration of arrangement of the treatment instrument insertion paths or a positional relationship with the ultrasound scattering portion provided on the puncture needle that is the treatment instrument inserted through the treatment instrument insertion path.

A further example of an arrangement form of ultrasound scattering portions on the over tube other than those shown in the above described examples will be now described.

Figure 29:
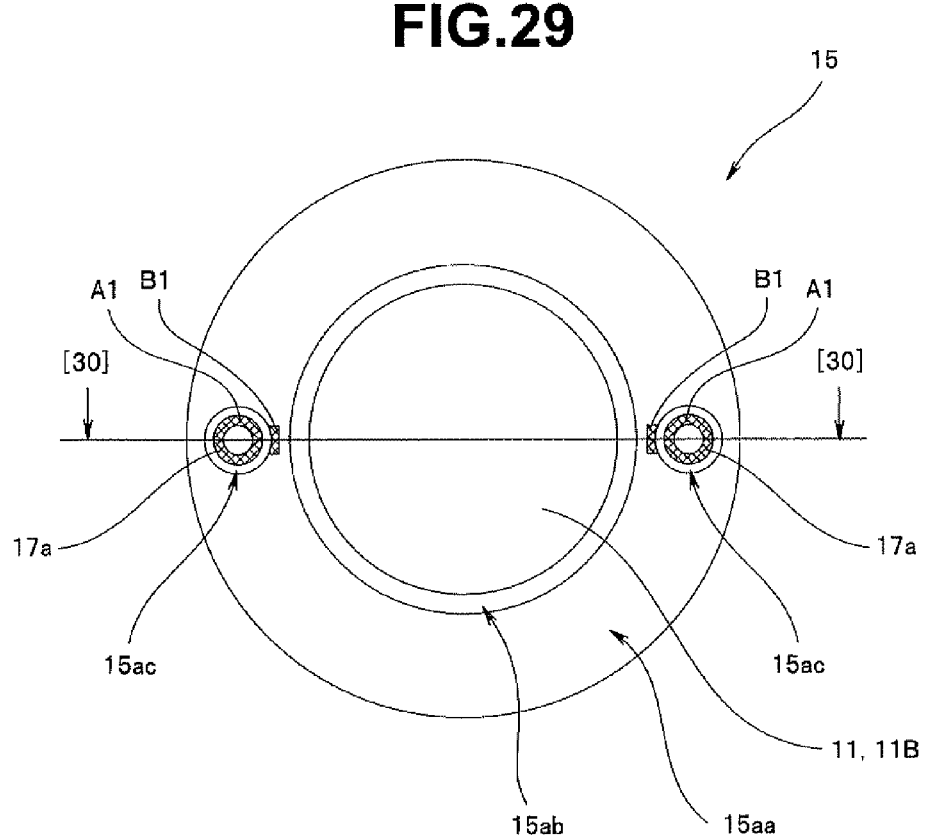
FIG. 29 is a front view of a distal end surface of an over tube in a further different arrangement form of ultrasound scattering portions at a distal end portion of the over tube in the treatment instrument system according to the present invention.
Figure 30:
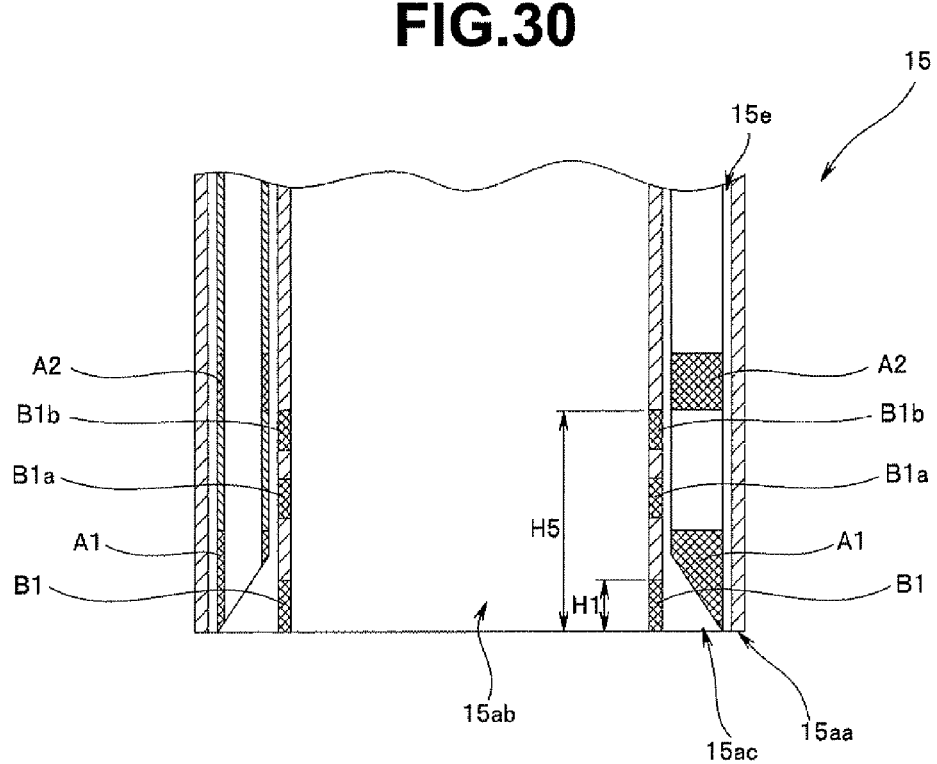
FIG. 30 is a cross-sectional view taken along the line [30]-[30] in FIG. 29.

FIGS. 29 and 30 show a further arrangement form of ultrasound scattering portions provided at the distal end portion of the over tube in the treatment instrument system according to the present invention, FIG. 29 is a front view of the distal end surface of the over tube, and FIG. 30 is a cross-sectional view taken along the line [30]-[30] in FIG. 29. In FIG. 30, as in FIGS. 3, 12 and 13, a puncture needle 17a inserted through a treatment instrument insertion path 15e is shown in side view in the right half.

In the arrangement form of the ultrasound scattering portions on the over tube in this example, the ultrasound scattering portions are placed in a plurality of positions in a longitudinal direction from the distal end surface of the over tube.

Specifically, as shown in FIG. 29, when viewed from the front of the distal end surface 15aa of the over tube 15, the ultrasound scattering portions are provided in substantially the same area as the above described section [D] in FIG. 20, that is, in a predetermined range in an area that is the part of the peripheral edge of the treatment instrument insertion opening 15ac in the over tube 15 and closer to the inner side, that is, a range of a longitudinal size H1 from the distal end surface 15aa of the over tube 15 as shown in FIG. 30.

Besides, as shown in the section in FIG. 30, at a peripheral edge of the treatment instrument insertion opening 15ac, an ultrasound scattering portion B1a is provided in substantially the same area as the area B1 and in a predetermined range at a predetermined distance from the area B1 in the longitudinal direction, and an ultrasound scattering portion B1b is further provided in substantially the same area as the area B1a and in a predetermined range at a predetermined distance from the area B1a in the longitudinal direction.

Specifically, in a range denoted by reference numeral H5 in FIG. 30, the ultrasound scattering portions are placed in a plurality of positions. Also with such an arrangement form, all the ultrasound scattering portions A1, A2, B1, B1a and B1b can be reliably checked with an ultrasound tomogram.

As disclosed in the above described embodiments and the examples in FIGS. 18 to 30, various arrangement forms of the treatment instrument insertion paths 15e, the treatment instrument insertion openings 15ac, and the ultrasound scattering portions can be supposed.

The ultrasound scattering portion provided at the distal end portion of the over tube or the treatment instrument is achieved by, for example, machining a surface of a predetermined area. Thus, it can be supposed that the ultrasound scattering portion on the over tube and the ultrasound scattering portion on the treatment instrument are differently processed. If the ultrasound scattering portions are differently processed depending on the areas on which the ultrasound scattering portions are provided, the ultrasound scattering portion on the over tube and the ultrasound scattering portion on the treatment instrument can be easily distinguished on the ultrasound tomogram.

The sectional shapes of the treatment instrument insertion paths of the over tube disclosed in the above described embodiments and the examples in FIGS. 18 to 30 are formed in a longitudinal direction of the over tube. But not limited thereto, for example, the sectional shape may be as shown in FIG. 31.

Figure 31:
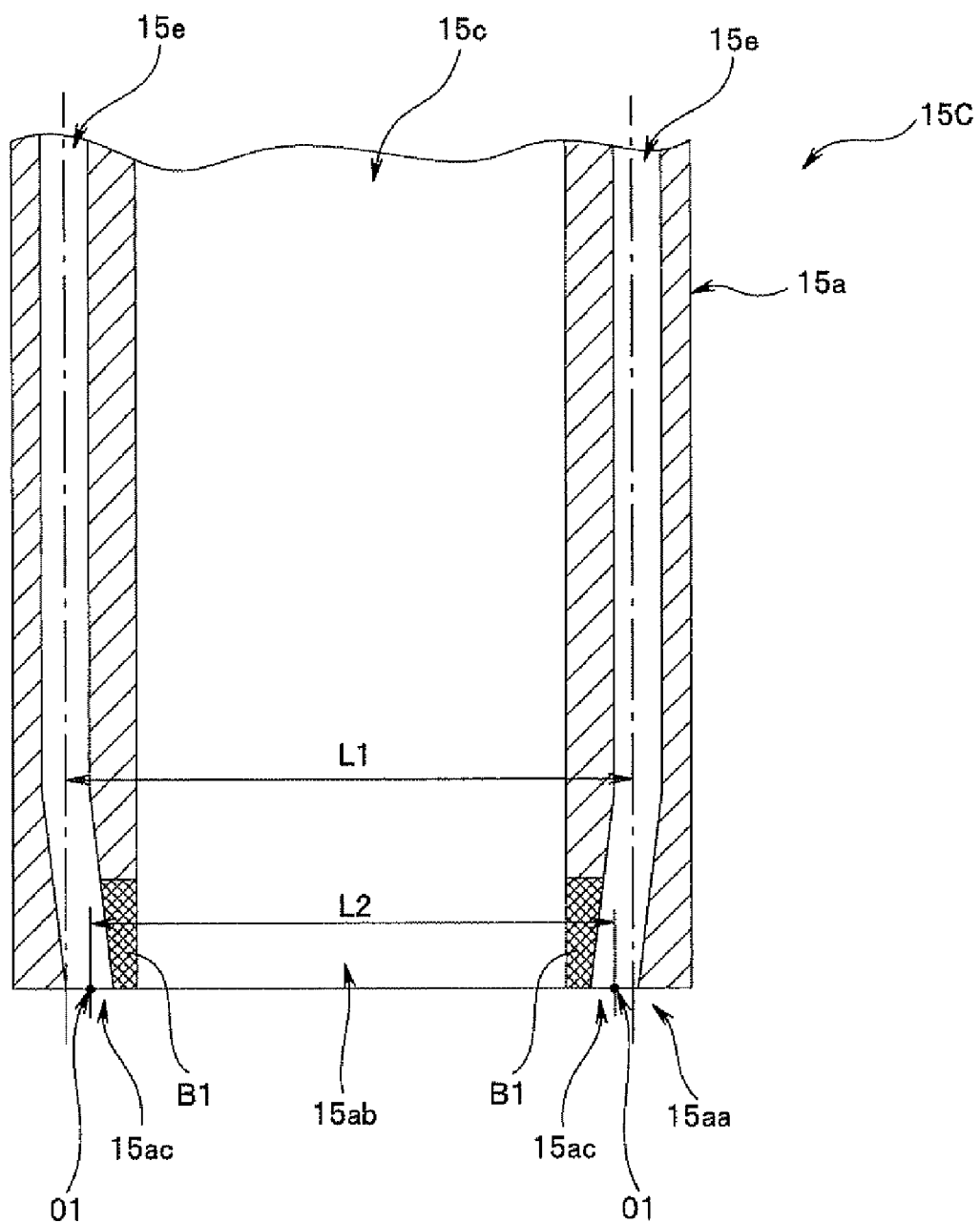
FIG. 31 is a cross-sectional view of a shape of a distal end portion of a treatment instrument insertion path through which the over tube is inserted in the treatment instrument system according to the present invention.

FIG. 31 is a cross-sectional view of a shape of a distal end portion of a treatment instrument insertion path through which an over tube is inserted in the treatment instrument system according to the present invention.

An over tube 15C in the example includes two treatment instrument insertion paths 15e that each communicate with a proximal end insertion path opening 15d (not shown in FIG. 31; see FIG. 1), pass through a flexible tube 15a, and reach a treatment instrument insertion opening 15ac opening in a distal end surface 15aa as in the above described embodiments.

The treatment instrument insertion paths 15e of the over tube 15C in the example are formed to have sections bending at a predetermined angle so as not to be parallel with each other at a distal end portion of the over tube 15C as shown in FIG. 31. The treatment instrument insertion opening 15ac is formed within a range of the distal end surface 15aa.

In other words, in the arrangement position of the two treatment instrument insertion openings 15ac, a distance L2 between center points O1 of the treatment instrument insertion openings 15ac is smaller than a distance L1 between center lines in a longitudinal direction of the treatment instrument insertion paths 15e.

In the example in FIG. 31, the treatment instrument insertion paths 15e in the over tube 15C are formed to bend toward the center of the over tube 15c at the distal end portion. However, not limited thereto, the treatment instrument insertion paths 15e may be formed to bend outward.

The treatment instrument insertion paths 15e are formed to bend at the distal end portion of the over tube 15C, and thus can accommodate various types of ultrasound endoscopes or probes placed through the ultrasound endoscope insertion path 15c. This allows ultrasound tomograms with higher definition to be obtained, and allows an efficient procedure or treatment performed using the treatment instrument system according to the present invention.

Next, a treatment instrument system according to a third embodiment of the present invention will be now described.

Figure 32:
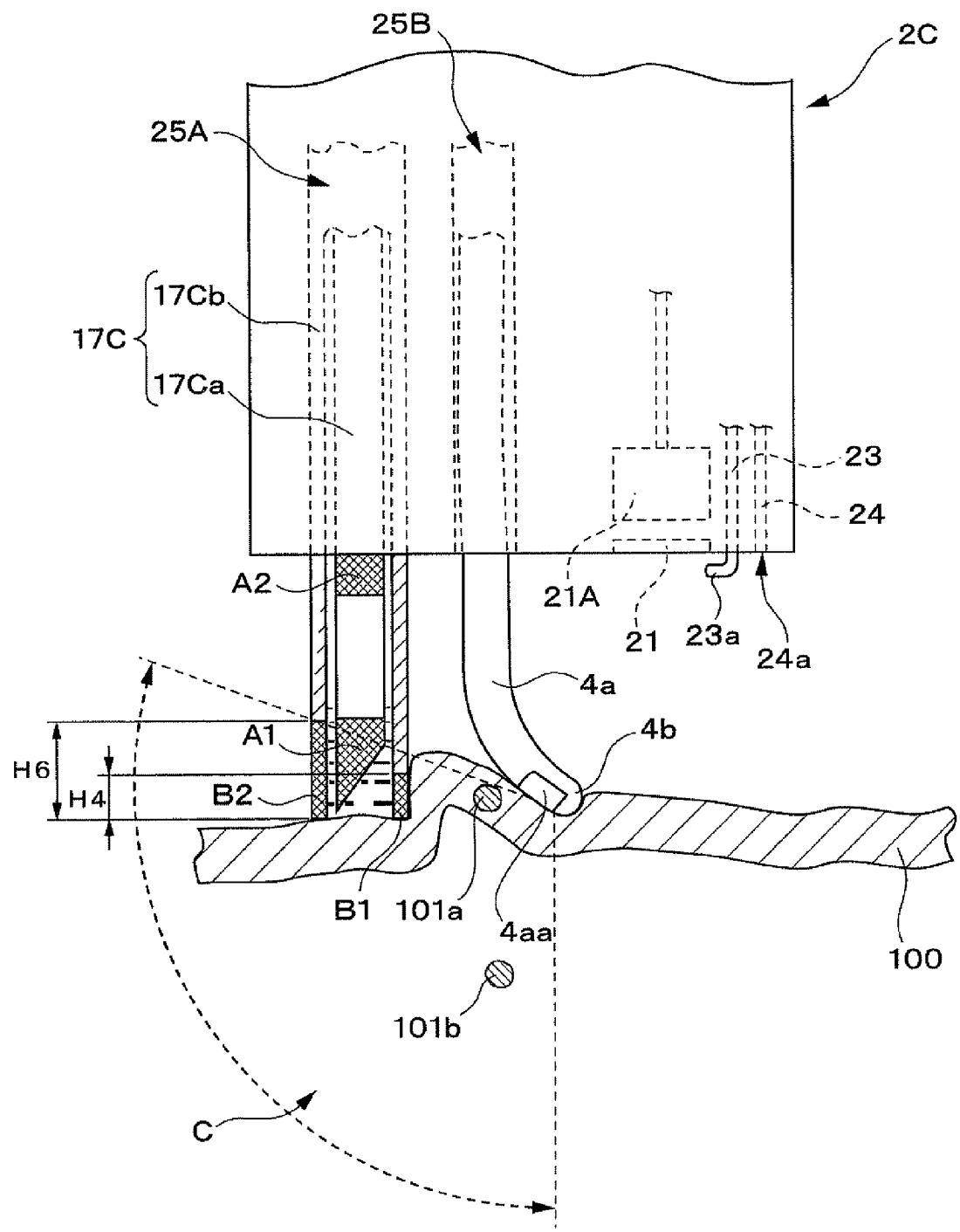
FIG. 32 is an enlarged view of essential portions of a distal end portion of an endoscope in an endoscope apparatus to which a treatment instrument system according to a third embodiment of the present invention is applied.

FIG. 32 is an enlarged view of essential portions of a distal end portion of an endoscope in an endoscope apparatus to which the treatment instrument system according to the third embodiment of the present invention is applied. FIG. 32 shows a configuration and a state of use of the distal end portion.

The first and second embodiments exemplify the treatment instrument system suitable for using a treatment instrument (such as a T-bar driver 17) for performing insufflation or suture treatment under observation of ultrasound tomograms. On the other hand, the present embodiment exemplifies a treatment instrument system suitable for using a treatment instrument that is placed through a treatment instrument channel of an endoscope for use, under observation of ultrasound tomograms.

The treatment instrument system according to the present embodiment includes an endoscope apparatus as used in the first embodiment, a treatment instrument 17C of various types placed through one treatment instrument channel 25A of an endoscope 2C in the endoscope apparatus for use, and an ultrasound probe 4a placed through the other treatment instrument channel 25B for use as shown in FIG. 32.

In the present embodiment, as shown in FIG. 32, the endoscope 2C in the endoscope apparatus includes the two treatment instrument channels 25A and 25B. The treatment instrument 17C for performing various types of treatment is placed through one of the two treatment instrument channels 25A and 25B of the endoscope 2C, and the ultrasound probe 4a is placed through the other.

In a distal end surface of an insertion portion of the endoscope 2C, an observation window 21, an illumination window, a water feeding nozzle 23a to be a water jetting portion, a suction air feeding opening 24a, or the like are provided. Inside the observation window 21, an image pickup unit 21A contributing to creating endoscopic observation images is provided.

The endoscope 2C in the present embodiment includes the two treatment instrument channels 25A and 25B, and thus two treatment instrument insertion openings (see reference numeral 12e in FIG. 1) communicating with the treatment instrument channels 25A and 25B, respectively, are provided in predetermined areas, for example, in an operation portion, though not shown.

Alternatively, for example, one treatment instrument insertion opening (12e) may be provided, in which an insertion path is bifurcated to communicate with the treatment instrument channels 25A and 25B, respectively.

Other configurations are substantially the same as the endoscope 2 in the treatment instrument system according to the first embodiment.

Through one of the treatment instrument channels 25A and 25B of the endoscope 2C, an ultrasound probe 4a as used in the first embodiment is placed. FIG. 32 shows an example in which the ultrasound probe 4a is placed through the treatment instrument channel 25B.

Through the other of the treatment instrument channels 25A and 25B, the treatment instrument 17C including a puncture needle 17Ca and a sheath 17Cb is placed. FIG. 32 shows an example in which the treatment instrument 17C is placed through the treatment instrument channel 25A.

The puncture needle 17Ca in the treatment instrument 17C is constituted by a flexible elongated tube and has a distal end formed into a sharp needle. To a proximal end (not shown in FIG. 32; see FIG. 1) of the puncture needle 17Ca, a control box is connected for controlling a protruding and retracting operation of the puncture needle 17Ca. To the control box, a gas/drug supplier 17e is connected for supplying gas (for example, carbon dioxide) or a liquid such as a drug via a hollow portion of the puncture needle 17Ca into an abdomen cavity.

On a distal end portion of the puncture needle 17Ca, a plurality of (two in the present embodiment in FIG. 32) ultrasound scattering portions A1 and A2 for scattering ultrasound are provided at predetermined intervals. The ultrasound scattering portion A1 is provided at a most distal end portion of the puncture needle 17Ca. The second ultrasound scattering portion A2 is provided at a predetermined distance from the ultrasound scattering portion A1 in a longitudinal direction of the puncture needle 17Ca.

The second ultrasound scattering portion A2 is provided for identifying a guide for a puncture depth of the puncture needle 17a. Thus, a distance between the ultrasound scattering portion A1 and the second ultrasound scattering portion A2 is freely set according to types of treatment and surgery.

The sheath 17Cb is constituted by a flexible elongated tube and can be inserted from a treatment instrument insertion opening (not shown) in an operation portion (not shown). The puncture needle 17Ca is inserted through a hollow tube of the sheath 17Cb. In this case, the puncture needle 17Ca is placed so as to be protruded from or retracted into the sheath 17Cb.

At a distal end portion of the sheath 17Cb, ultrasound scattering portions B1 and B2 as on the puncture needle 17Ca are provided in a predetermined range.

The ultrasound scattering portions B1 and B2 are each provided in a predetermined range in a longitudinal direction of the treatment instrument channel 25A from the distal end toward the proximal end of the sheath 17Cb. In this case, the longitudinal range (in an insertion direction) of the ultrasound scattering portion B1 is set to be smaller than a longitudinal range of the ultrasound scattering portion B2.

Specifically, in FIG. 32, the range is set so that a relationship of H4<H6 is satisfied where H4 is a length (referred to as an axial length) of the longitudinal range of the ultrasound scattering portion B1, and H6 is a length (referred to as an axial length) of the longitudinal range of the ultrasound scattering portion B2.

In other words, the distal end of the sheath 17Cb is formed so that the axial lengths of the ultrasound scattering portions B1 and B2 are circumferentially different.

Figure 33:
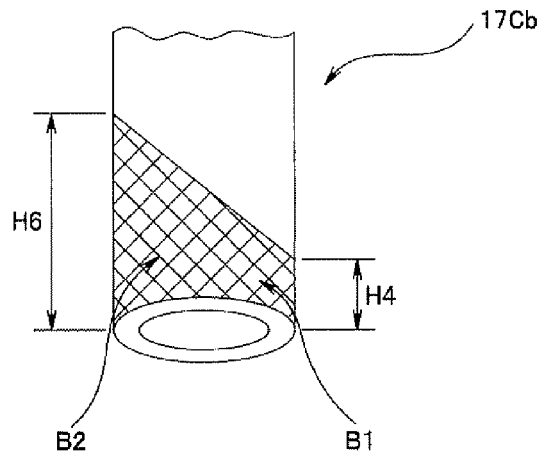
FIG. 33 shows a first arrangement example of ultrasound scattering portions provided at a distal end of a sheath in the endoscope apparatus in FIG. 32.
Figure 34:
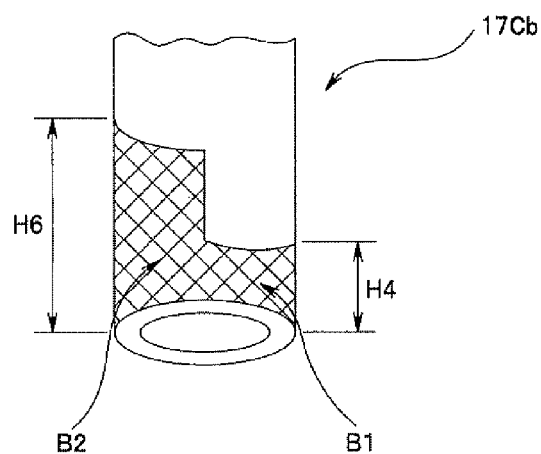
FIG. 34 shows a second arrangement example of ultrasound scattering portions provided at the distal end of the sheath in the endoscope apparatus in FIG. 32.
Figure 35:
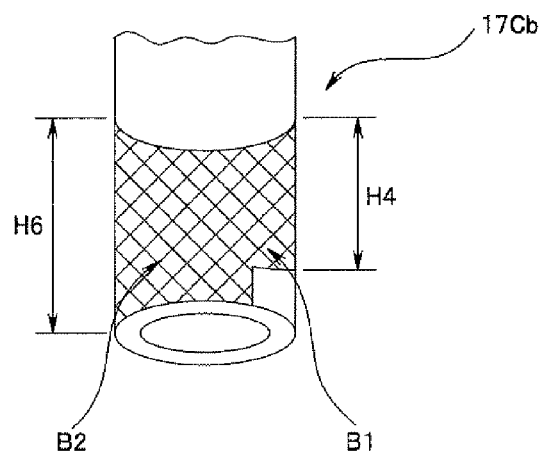
FIG. 35 shows a third arrangement example of ultrasound scattering portions provided at the distal end of the sheath in the endoscope apparatus in FIG. 32.

The ultrasound scattering portions B1 and B2 provided at the distal end of the sheath 17Cb have forms, for example, as shown in FIGS. 33, 34 and 35. In this case, the ultrasound scattering portions B1 and B2 are formed on an outer peripheral surface of the distal end of the sheath 17Cb. In FIGS. 33, 34 and 35, cross-hatched areas represent the ultrasound scattering portions B1 and B2.

In a first example in FIG. 33, the ultrasound scattering portions B1 and B2 are circumferentially formed on the outer peripheral surface of the distal end when the sheath 17Cb is viewed substantially from a side. In this case, an area extending from an area of the ultrasound scattering portion B1 to an area of the ultrasound scattering portion B2 is connected by a line inclined with respect to an axial direction so that axial lengths denoted by reference numerals H4 and H6 are different between the area B1 and the area B2, and a relationship of the axial lengths H4<H6 is satisfied.

In a second example in FIG. 34, the ultrasound scattering portions B1 and B2 are similarly circumferentially formed on the outer peripheral surface of the distal end when the sheath 17Cb is viewed substantially from a side. In this case, a step is formed between an area of the ultrasound scattering portion B1 and an area of the ultrasound scattering portion B2 so that axial lengths denoted by reference numerals H4 and H6 are different between the area B1 and the area B2, and a relationship of the axial lengths H4<H6 is satisfied.

In a third example in FIG. 35, the ultrasound scattering portions B1 and B2 are similarly circumferentially formed on the outer peripheral surface of the distal end when the sheath 17Cb is viewed substantially from a side. In this case, there is an area without an ultrasound scattering portion in a part of an area of the ultrasound scattering portion B1, that is, a part of a predetermined area from a most distal end of the sheath 17Cb. Thus, axial lengths denoted by reference numerals H4 and H6 are different in FIG. 35, and a relationship of the axial lengths H4<H6 is satisfied.

The sheath 17Cb is placed through the treatment instrument channel 25A so as to be freely protruded and retracted and be rotatable. Thus, when performing an operation for inserting the treatment instrument 17C through the treatment instrument channel 25A, the operator cannot recognize the positions of the ultrasound scattering portions B1 and B2 provided at the distal end portion of the sheath 17Cb of the treatment instrument 17C. On the other hand, inserting the treatment instrument 17C through the treatment instrument channel 25A and placing the distal end portion thereof in a predetermined area at the distal end portion of the endoscope 2C is controlled from the relationship between the length of the treatment instrument 17C and the length of the treatment instrument channel 25A of the endoscope 2, and can be easily performed. Thus, the operator observes an ultrasound tomogram of the distal end portion of the endoscope 2C using the ultrasound probe 4a placed through the treatment instrument channel 25B with the distal end portion of the treatment instrument 17C being placed in a predetermined position on the distal end portion of the treatment instrument channel 25A, and thus the ultrasound scattering portions A1, A2, B1 and B2 provided at the distal end portions of the sheath 17Cb and the puncture needle 17Ca can be placed in predetermined positions.

An outline of a process of treatment of an organ in an abdomen cavity by the NOTES procedure using the treatment instrument system thus configured according to the present embodiment will be now described.

First, the endoscope 2C is inserted through a natural orifice, for example, an oral cavity of a subject (patient) to undergo surgery into a target luminal organ, for example, a stomach under observation of endoscopic images. In this case, an insertion operation of the endoscope 2C is similar to an operation for a flexible endoscope examination generally performed.

With the distal end of the endoscope 2C being inserted into the luminal organ (stomach), the ultrasound probe 4a is placed through one of the treatment instrument channels 25A and 25B, and the treatment instrument 17C is placed through the other.

Then, the distal end portion of the ultrasound probe 4a is protruded from the distal end surface of the endoscope 2C, and positioned so that an ultrasound transmitting and receiving surface of the ultrasound unit 4aa provided in the distal end portion is substantially brought into tight contact with the stomach wall 100. In this state, an ultrasound observing apparatus (not shown) is operated to drive and control the ultrasound probe 4a. Thus, ultrasound tomograms of the stomach wall 100, an organ in an abdomen cavity or blood vessels outside the stomach wall 100, and the treatment instrument 17C are displayed on the display apparatus.

For obtaining the ultrasound tomograms using the ultrasound probe 4a and the ultrasound observing apparatus in the treatment instrument system according to the present embodiment, as shown in FIG. 32, tissue in a body cavity or an unshown balloon is placed between the ultrasound unit 4aa at the distal end portion of the ultrasound probe 4a and the target subject. Thus, ultrasound transmitted from the ultrasound unit 4aa is reliably transmitted to the target subject, and reflected waves can be received by the ultrasound unit 4aa. Thus, ultrasound tomograms of a desired area, that is, the stomach wall 100, an organ in an abdomen cavity or blood vessels outside the stomach wall, and the ultrasound scattering portion on the treatment instrument 17C are displayed on the display apparatus 5a so as to be visually observed.

Under observation of the ultrasound tomograms and the endoscopic images, the operator operates the ultrasound probe 4a, and searches and identifies an area suitable for puncture of the puncture needle 17Ca, that is, a safe puncture start position where organs in an abdomen cavity or blood vessels are not damaged.

When the puncture start position is identified, the distal end portion of the treatment instrument 17C is protruded from the distal end surface of the endoscope 2C, and then the distal end of the sheath 17Cb of the treatment instrument 17C is abutted against the stomach wall 100 at the identified puncture start position.

Then, under observation of the ultrasound tomograms and the endoscopic images, the operator operates the ultrasound probe 4a to direct the ultrasound transmitting and receiving portion of the ultrasound unit 4aa at the distal end portion to a desired region.

Next, the operator sets so that the ultrasound transmitting and receiving portion of the ultrasound unit 4aa is directed to the distal end portion of the sheath 17Cb, and the ultrasound scattering portions B1 and B2 at the distal end of the sheath 17Cb are simultaneously displayed on the display apparatus as shown in FIG. 32.

Then, the operator protrudes the puncture needle 17Ca outward from the front surface of the sheath 17Cb. Thus, the distal end of the puncture needle 17Ca penetrates the stomach wall 100 and protrudes into an organ in the abdomen cavity. The puncturing operation of the puncture needle 17Ca is performed under observation of ultrasound tomograms. Thus, during the puncturing operation, the ultrasound scattering portion A1 of the puncture needle 17Ca advancing an area between the ultrasound scattering members B1 and B2 is observed on the ultrasound tomograms. In this case, a desired puncture depth of the puncture needle 17Ca can be recognized by observing, on the display screen of the ultrasound tomograms, a position of the second ultrasound scattering portion A2 on the back side at a distance in a longitudinal direction from the ultrasound scattering portion A1 at the distal end, among the two ultrasound scattering portions A1 and A2 on the puncture needle 17Ca. Thus, the operator observes the ultrasound tomograms while performing the puncturing operation of the puncture needle 17Ca, and stops the puncturing operation when the ultrasound scattering portions A1 and A2 on the puncture needle 17Ca reach desired positions.

Thus, the distal end portion of the puncture needle 17Ca penetrates the stomach wall 100 and protrudes into the organ in the abdomen cavity by a predetermined length. In this state, for example, the operator operates the control box at hand to control the gas/drug supplier 17e to perform a drug supply operation from the puncture needle 17Ca into the organ in the abdomen cavity, or take tissue in the organ in the abdomen cavity.

After the desired treatment is completed, the operator operates the control box to draw the puncture needle 17Ca into the sheath 17Cb, and draw the sheath 17Cb into the treatment instrument channel. After the ultrasound probe 4a is drawn into the treatment instrument channel, the endoscope 2C is removed from the luminal organ.

As described above, in the third embodiment, the ultrasound scattering portions are provided in the predetermined areas at the distal end portion of the treatment instrument 17C including the puncture needle 17Ca and the sheath 17Cb, and thus the position of the treatment instrument 17C can be reliably checked on the ultrasound tomograms when treatment of an organ in an abdomen cavity is performed under observation of ultrasound tomograms. This allows treatment on an organ or blood vessels in an abdomen cavity that cannot be observed on the endoscopic images to be performed with higher safety.

The treatment instrument system has a configuration capable of performing treatment without an over tube, thereby simplifying the entire system and allowing a convenient operation.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. A treatment instrument system comprising:
an endoscope having a treatment instrument channel;
an ultrasound probe inserted through the treatment instrument channel of the endoscope;
an ultrasound observing apparatus having a blood flow display function and a distance measuring function;
a treatment instrument having, at a distal end portion, a first ultrasound scattering portion for scattering ultrasound; and
an over tube having an endoscope insertion path through which the endoscope can be inserted and a treatment instrument insertion path through which the treatment instrument can be inserted, and having, at a distal end portion, a second ultrasound scattering portion configured to enable identification of a moving direction of the first ultrasound scattering portion and identification of a relative position of the first ultrasound scattering portion with respect to the second ultrasound scattering portion on an ultrasound tomogram.

2. The treatment instrument system according to claim 1, wherein the first ultrasound scattering portion on the treatment instrument is provided on an outer periphery of a most distal end portion of the treatment instrument.

3. The treatment instrument system according to claim 2, wherein the treatment instrument has a third ultrasound scattering portion at a predetermined distance from an area where the first ultrasound scattering portion is provided.

4. The treatment instrument system according to claim 2, wherein the treatment instrument is a suture treatment instrument for suturing a dissected region.

5. The treatment instrument system according to claim 1, wherein the second ultrasound scattering portion on the over tube is provided at a peripheral edge of a distal end portion of the treatment instrument insertion path.

6. The treatment instrument system according to claim 5, wherein the second ultrasound scattering portion on the over tube is provided entirely around an outer periphery of the treatment instrument insertion path at the peripheral edge of the distal end portion of the treatment instrument insertion path.

7. The treatment instrument system according to claim 5, wherein the second ultrasound scattering portion on the over tube is provided in a part of an area at the peripheral edge of the distal end portion of the treatment instrument insertion path.

8. The treatment instrument system according to claim 7, wherein the part of the area at the peripheral edge of the distal end portion of the treatment instrument insertion path is an area closer to the endoscope insertion path of the over tube.

9. The treatment instrument system according to claim 7, wherein the part of the area at the peripheral edge of the distal end portion of the treatment instrument insertion path is an area closer to the endoscope insertion path of the over tube and an area closer to an outer peripheral surface of the over tube.

10. The treatment instrument system according to claim 9, wherein an axial forming area of the endoscope insertion path in the second ultrasound scattering portion provided in the area closer to the endoscope insertion path of the over tube is smaller than an axial forming area of the endoscope insertion path in the second ultrasound scattering portion provided in the area closer to the outer peripheral surface of the over tube.

11. The treatment instrument system according to claim 1, wherein the treatment instrument is a suture treatment instrument for suturing a dissected region.

12. A treatment instrument system comprising:
an ultrasound endoscope having a treatment instrument channel;
an ultrasound observing apparatus having a blood flow display function and a distance measuring function;
a treatment instrument having, at a distal end portion, a first ultrasound scattering portion for scattering ultrasound; and
an over tube having an endoscope insertion path through which the ultrasound endoscope can be inserted and a treatment instrument insertion path through which the treatment instrument can be inserted, and having, at a distal end portion, a second ultrasound scattering portion configured to enable identification of a moving direction of the first ultrasound scattering portion and identification of a relative position of the first ultrasound scattering portion with respect to the second ultrasound scattering portion on an ultrasound tomogram.

13. The treatment instrument system according to claim 12, wherein the first ultrasound scattering portion on the treatment instrument is provided on an outer periphery of a most distal end portion of the treatment instrument.

14. The treatment instrument system according to claim 13, wherein the treatment instrument has a third ultrasound scattering portion at a predetermined distance from an area where the first ultrasound scattering portion is provided.

15. The treatment instrument system according to claim 12, wherein the second ultrasound scattering portion on the over tube is provided at a peripheral edge of a distal end portion of the treatment instrument insertion path.

16. The treatment instrument system according to claim 15, wherein the second ultrasound scattering portion on the over tube is provided entirely around an outer periphery of the treatment instrument insertion path at the peripheral edge of the distal end portion of the treatment instrument insertion path.

17. The treatment instrument system according to claim 15, wherein the second ultrasound scattering portion on the over tube is provided in a part of an area at the peripheral edge of the distal end portion of the treatment instrument insertion path.

18. The treatment instrument system according to claim 17, wherein the part of the area at the peripheral edge of the distal end portion of the treatment instrument insertion path is an area closer to the endoscope insertion path of the over tube.

19. The treatment instrument system according to claim 17, wherein the part of the area at the peripheral edge of the distal end portion of the treatment instrument insertion path is an area closer to the endoscope insertion path of the over tube and an area closer to an outer peripheral surface of the over tube.

20. The treatment instrument system according to claim 19, wherein an axial forming area of the endoscope insertion path in the second ultrasound scattering portion provided in the area closer to the endoscope insertion path of the over tube is smaller than an axial forming area of the endoscope insertion path in the second ultrasound scattering portion provided in the area closer to the outer peripheral surface of the over tube.

21. A treatment instrument system comprising:
an endoscope having a plurality of treatment instrument channels;
an ultrasound probe placed through one of the treatment instrument channels of the endoscope;
an ultrasound observing apparatus having a blood flow display function and a distance measuring function;
a treatment instrument having, at an distal end portion, a first ultrasound scattering portion for scattering ultrasound; and
a sheath member having a treatment instrument insertion path through which the treatment instrument can be inserted, having, at a distal end portion, a second ultrasound scattering portion configured to enable identification of a moving direction of the first ultrasound scattering portion and identification of a relative position of the first ultrasound scattering portion with respect to the second ultrasound scattering portion on an ultrasound tomogram, and placed through another of the treatment instrument channels of the endoscope.

22. The treatment instrument system according to claim 21, wherein the second ultrasound scattering portion on the treatment instrument is provided on an outer periphery of a most distal end portion of the treatment instrument.

23. The treatment instrument system according to claim 22, wherein the treatment instrument has a third ultrasound scattering portion at a predetermined distance from an area where the first ultrasound scattering portion is provided.

24. The treatment instrument system according to claim 21, wherein the second ultrasound scattering portion on the sheath member is provided entirely around an outer periphery of a distal end of the sheath member.

25. The treatment instrument system according to claim 21, wherein the distal end of the sheath member is formed so that an axial length of the second ultrasound scattering portion is circumferentially different.

26. The treatment instrument system according to claim 21, wherein the treatment instrument is a suture treatment instrument for suturing a dissected region.

* * * * *